United States Patent [19]

Kawai et al.

[11] Patent Number: 5,670,503
[45] Date of Patent: Sep. 23, 1997

[54] PYRAZOLE DERIVATIVES

[75] Inventors: Yoshio Kawai, Ushiku; Hitoshi Yamazaki, Tsukuba; Hirokazu Tanaka, Takarazuka; Teruo Oku, Tsukuba, all of Japan

[73] Assignee: Fujisawa Pharmaceutical Co., Ltd., Osaka, Japan

[21] Appl. No.: 505,284

[22] PCT Filed: Feb. 9, 1994

[86] PCT No.: PCT/JP94/00213

§ 371 Date: Aug. 21, 1995

§ 102(e) Date: Aug. 21, 1995

[87] PCT Pub. No.: WO94/19350

PCT Pub. Date: Sep. 1, 1994

[30] Foreign Application Priority Data

Feb. 26, 1993 [GB] United Kingdom .................. 9303993

[51] Int. Cl.⁶ .................... C07D 251/72; C07D 253/10
[52] U.S. Cl. .......................................... 514/243; 544/183
[58] Field of Search ............................ 514/243; 544/183

[56] References Cited

U.S. PATENT DOCUMENTS 5,356,897 10/1994 Oku et al. ................................ 514/258

OTHER PUBLICATIONS

Ruddle et al; *J. Exp. Med.;* Oct. 1990; 172, 1193–1200.

*Primary Examiner*—Mukund J. Shah
*Assistant Examiner*—Tamthom T. Ngo
*Attorney, Agent, or Firm*—Oblon, Spivak, McClelland, Maier & Neustadt, P.C.

[57] ABSTRACT

New heterocyclic derivatives of the formula:

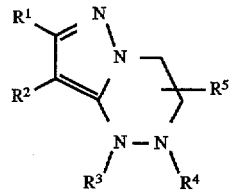

wherein
 $R^1$ is aryl which may have suitable substituent(s) or heterocyclic group which may have suitable substituent (s),
 $R^2$ is aryl which may have suitable substituent(s) or heterocyclic group which may have suitable substituent (s),
 $R^3$ is hydrogen or acyl,
 $R^4$ is hydrogen, lower alkyl, cyclo(lower)alkyl, cyclo (lower)alkyl-(lower)alkyl, carboxy(lower)alkyl, protected carboxy(lower)alkyl, ar(lower)alkyl which may have suitable substituent(s), ar(lower)alkenyl, bridged tricyclicalkyl, heterocyclic group which may have suitable substituent(s), acyl, or a group of the formula

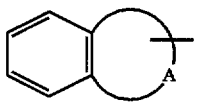

(in which A is lower alkylene), and
 $R^5$ is hydrogen or lower alkyl,
and a pharmaceutically acceptable salt thereof which are useful as a medicament.

12 Claims, No Drawings

PYRAZOLE DERIVATIVES

TECHNICAL FIELD

This invention relates to new heterocylic derivatives and pharmaceutically acceptable salts thereof which are useful as a medicament.

DISCLOSURE OF INVENTION

This invention relates to new heterocyclic derivatives. More particularly, this invention relates to pyrazole derivatives and pharmaceutically acceptable salts thereof which have pharmacological activities, processes for preparation thereof, a pharmaceutical composition comprising the same and a use of the same.

Accordingly, one object of this invention is to provide the new and useful pyrazole derivatives and pharmaceutically acceptable salts thereof which possess a strong inhibitory activity on the production of Interleukin-1 (IL-1) and a strong inhibitory activity on the production of tumor necrosis factor (TNF).

Another object of this invention is to provide processes for preparation of the pyrazole derivatives and salts thereof.

A further object of this invention is to provide a pharmaceutical composition comprising said pyrazole derivatives or a pharmaceutically acceptable salt thereof.

Still further object of this invention is to provide a use of said pyrazole derivatives or a pharmaceutically acceptable salt thereof as a medicament for prophylactic and therapeutic treatment of IL-1 and TNF mediated diseases such as chronic inflammatory diseases, specific autoimmune diseases, sepsis-induced organ injury, and the like in human being and animals.

The object pyrazole derivatives of the present invention are novel and can be represented by the following general formula (I):

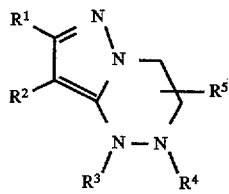

(I)

wherein
- $R^1$ is aryl which may have suitable substituent(s) or heterocyclic group which may have suitable substituent(s),
- $R^2$ is aryl which may have suitable substituent(s) or heterocyclic group which may have suitable substituent(s),
- $R^3$ is hydrogen or acyl,
- $R^4$ is hydrogen, lower alkyl, cyclo(lower)alkyl, cyclo(lower)alkyl-(lower)alkyl, carboxy(lower)alkyl, protected carboxy(lower)alkyl, ar(lower)alkyl which may have suitable substituent(s), ar(lower)alkenyl, bridged tricyclicalkyl, heterocyclic group which may have suitable substituent(s), acyl, or a group of the formula:

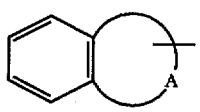

(in which A is lower alkylene), and
$R^5$ is hydrogen or lower alkyl.

The object compound (I) of the present invention can be prepared by the following processes.

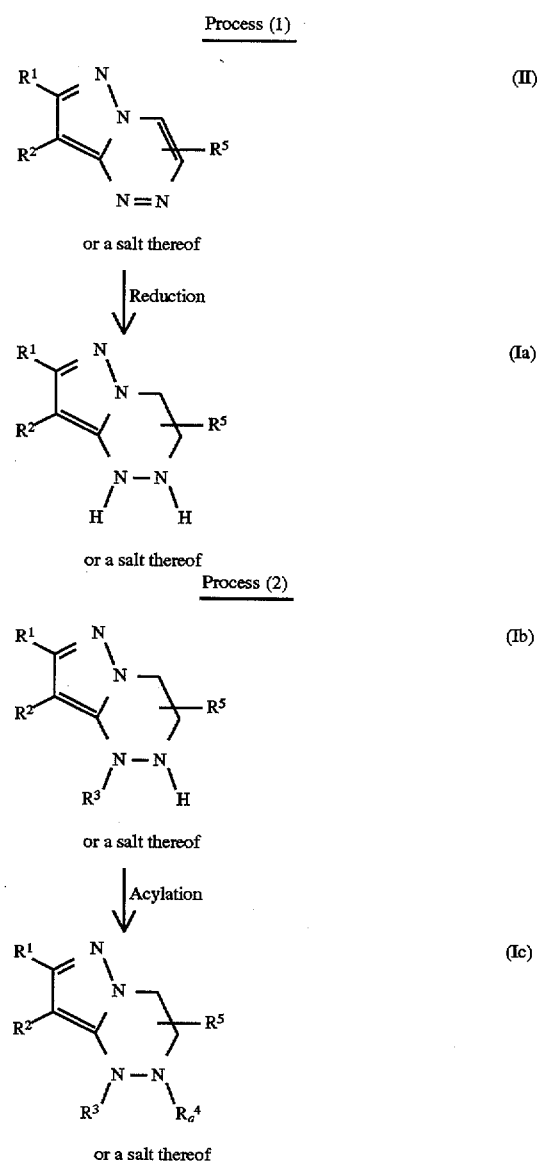

wherein
R$^1$, R$^2$, R$^3$ and R$^5$ are each as defined above,
R$_a^4$ is acyl,
R$_b^4$ is acyl having protected hydroxy,
R$_c^4$ is acyl having hydroxy,
R$_d^4$ is acyl having protected amino,
R$_e^4$ is acyl having amino, $R_f^4$ is acyl having a leaving group,
$R_g^4$ is acyl having N-containing heterocyclic group,
$R^6$ is hydrogen, $C_1$–$C_5$ alkyl, cyclo(lower)alkyl, cyclo(lower)alkyl-($C_1$–$C_5$)alkyl, aryl which may have suitable substituent(s) or ar($C_1$–$C_5$)alkyl which may have suitable substituent(s), a group of the formula:

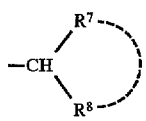

is lower alkyl, cyclo(lower)alkyl, cyclo(lower)alkyl-(lower)alkyl, carboxy(lower)alkyl, protected carboxy (lower)alkyl, ar (lower)alkyl which may have suitable substituent(s), ar (lower)alkenyl, bridged tricyclicalkyl, heterocyclic group which may have suitable substituent(s), or a group of the formula:

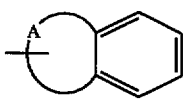

(in which A is lower alkylene),
$X^{1\ominus}$ is anion, and

is N-containing heterocyclic group.

The starting compounds or salts thereof can be prepared by the following Processes.

Process (A)

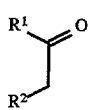

(V)
or a salt thereof

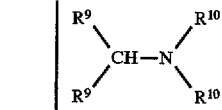

(VI)
or a salt thereof

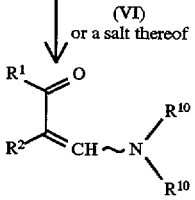

(VII)
or a salt thereof

-continued
Process (B)

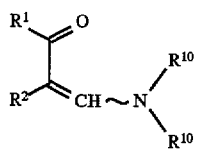

(VII)
or a salt thereof

↓ H$_2$NOH
(VIII)
or a salt thereof

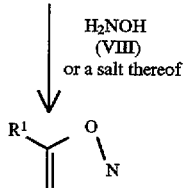

(IX)
or a salt thereof

Process (C)

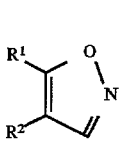

(IX)
or a salt thereof

↓ Cleavage reaction of O—N bond

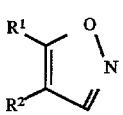

(X)
or a salt thereof

Process (D)

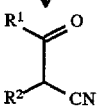

(X)
or a salt thereof

① ↓ halogenation

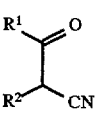

(XI)
or a salt thereof

② ↓ H$_2$NNH$_2$
(XII)
or a salt thereof

-continued

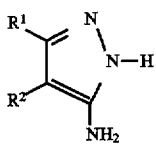

(XIII)
or a salt thereof

Process (E)

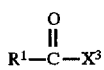

(XIV)
or a salt thereof

↓ R²—CH₂CN
(XV)
or a salt thereof

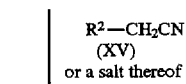

(X)
or a salt thereof

Process (F)

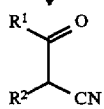

(X)
or a salt thereof

↓ NH₂NH₂
(XII)
or a salt thereof

(XIII)
or a salt thereof

Process (G)

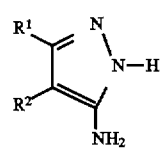

(XIII)
or a salt thereof

↓ diazotization

-continued

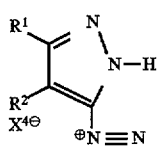

(XVI)
or a salt thereof

Process (H)

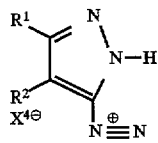

(XVI)
or a salt thereof

↓ (R¹¹)₃P=CH—COR⁵
(XVII)
or a salt thereof

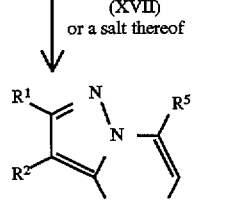

(IIa)
or a salt thereof

Process (I)

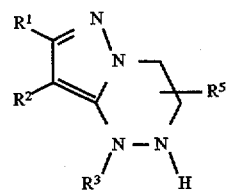

(Ib)
or a salt thereof

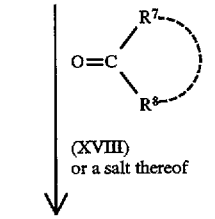

(XVIII)
or a salt thereof

↓

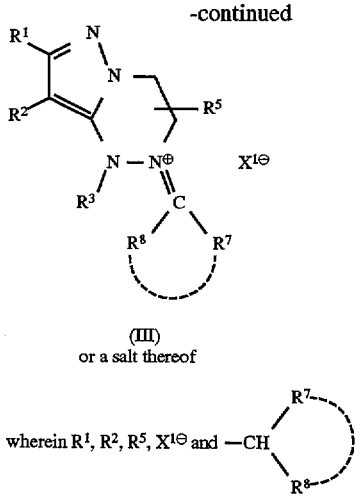

(III)
or a salt thereof wherein $R^1$, $R^2$, $R^5$, $X^{1\ominus}$ and $-CH\begin{pmatrix}R^7 \\ R^8\end{pmatrix}$ are each as defined above, $R^9$ and $X^3$ are each a leaving group, $X^2$ is halogen, $R^{10}$ is lower alkyl, $R^{11}$ is lower alkyl or aryl, and $X^4$ is acid residue.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt;

a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.);

an inorganic acid addition salt (e.g., hydrochloride, hydrobromide, sulfate, phosphate, etc.);

an organic carboxylic or sulfonic acid addition salt (e.g., formate, acetate, trifluoroacetate, maleate, tartrate, fumarate, methanesulfonate, benzenesulfonate, toluenesulfonate, etc.);

a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6 carbon atom(s), unless otherwise provided.

The term "higher" is used to intend a group having 7 to 20 carbon atoms, unless otherwise provided.

Suitable "lower alkyl" and "lower alkyl moiety" in the terms "cyclo(lower)alkyl-(lower)alkyl", "carboxy(lower)alkyl", "protected carboxy(lower)alkyl" and "ar(lower)alkyl" may include straight or branched one having 1 to 6 carbon atoms(s), such as methyl, ethyl, propyl, isopropyl, butyl, isobutyl, sec-butyl, tert-butyl, pentyl, neopentyl, tert-pentyl, hexyl, 1,1-dimethylbutyl, 2,2-dimethylbutyl, and the like.

Suitable "lower alkenyl moiety" in the term "ar(lower)alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)-methyl-1-(or 2- or 3-)butenyl, and the like, in which more preferable example may be $C_2$–$C_4$ alkenyl.

Suitable "protected amino" and "protected amino moiety" in the term "acyl having protected amino" may include an acylamino or an amino group substituted by a conventional protecting group such as ar(lower)alkyl which may have suitable substituent(s)(e.g., benzyl, trityl, etc.) or the like.

Suitable "acyl" and "acyl moiety" in the term "acylamino", "acyl having protected hydroxy", "acyl having hydroxy", "acyl having protected amino", "acyl having amino", "acyl having a leaving group" and "acyl having N-containing heterocyclic group" may include carbamoyl, cyclo(lower)alkylcarbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carbamoyl; Thiocarbamoyl;

cyclo(lower)alkylcarbonyl (e.g., cyclopropylcarbonyl, cyclohexylcarbonyl, etc.);

Aliphatic acyl such as lower or higher alkanoyl(e.g., formyl, acetyl, propanoyl, isobutyryl, butanoyl, pivaloyl, 2-methylpropanoyl, pentanoyl, 2,2-dimethylpropanoyl, 3,3-dimethylbutanoyl, 2,2-dimethylbutanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, isobutyloxycarbonyl, t-butoxycarbonyl, t-pentyloxycarbonyl, heptyloxycarbonyl, etc.);

lower alkoxyglyoxyloyl (e.g., methoxalyl, ethoxalyl, etc.), lower or higher alkylsulfonyl (e.g., methylsulfonyl, ethylsulfonyl, etc.);

lower or higher alkoxysulfonyl (e.g., methoxysulfonyl, ethoxysulfonyl, etc.); or the like.

Aromatic acyl such as aroyl (e.g., benzoyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower)alkenoyl (e.g., naphthylpropenoyl, naphthylbutenoyl, etc.), etc.];

ar(lower)alkoxycarbonyl [e.g. phenyl(lower) alkoxycarbonyl (e.g., benzyloxycarbonyl, etc.), etc.];

aryloxycarbonyl (e.g., phenoxycarbonyl, naphthyloxycarbonyl, etc.);

arylthio(lower)alkanoyl [e.g., phenylthio(lower)alkanoyl (e.g., phenylthioacetyl, phenylthiopropanoyl, etc.), etc.];

aryloxy(lower)alkanoyl (e.g., phenoxyacetyl, phenoxypropionyl, etc.);

arylcarbamoyl (e.g., phenylcarbamoyl, etc.);

aryl-thiocarbamoyl (e.g., phenyl-thiocarbamoyl, etc.);

arylglyoxyloyl (e.g., phenylglyoxyloyl, naphthylglyoxyloyl, etc.);

arylsulfonyl (e.g., phenylsulfonyl, p-tolylsulfonyl, etc.); or the like;

Heterocyclic acyl such as heterocycliccarbonyl; heterocycliccarbamoyl; heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.); heterocyclicglyoxyloyl; or the like;

in which suitable "heterocyclic moiety" in the terms "heterocycliccarbonyl", "heterocycliccarbamoyl", "heterocyclic(lower)alkyl", heterocyclic(lower) alkenoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered(more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1, 2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered)heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s)and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s)and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

saturated 3 to 8-membered (more preferably 5 or 6-membered) heteromonocyclic group containing 1 to 2 oxygen atom(s), for example, tetrahydrofuryl, tetrahydropyranyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

spiro heterocyclic group containing 1 to 2 oxygen atom (s), for example, dioxaspiroundecanyl (e.g., 1,5-dioxaspiro[5,5]undecanyl, etc.), etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example benzoxathiinyl, etc.; and the like.

The acyl moiety as stated above may have one to ten, same or different, suitable substituent(s) such as lower alkyl (e.g., methyl, ethyl, propyl, etc.); lower alkoxy (e.g., methoxy, ethoxy, propoxy, etc.); lower alkylthio (e.g., methylthio, ethylthio, etc.); lower alkylamino (e.g., methylamino, ethylamino, propylamino, etc.); mono (or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), di(lower)alkylamino (e.g. dimethylamino, diethylamino, etc.); cyclo(lower)alkyl (e.g., cyclopropyl, cyclopentyl, cyclohexyl, etc.); cyclo(lower)alkenyl (e.g., cyclohexenyl, cyclohexadienyl, etc.); halogen (e.g., fluorine, chlorine, bromine, iodine); amino, protected amino as mentioned above; hydroxy; protected hydroxy as mentioned below; cyano; nitro; carboxy; protected carboxy as mentioned below; sulfo; aryl (e.g., phenyl, naphthyl, etc.); sulfamoyl; imino; oxo; amino(lower)alkyl (e.g., aminomethyl, aminoethyl, etc.); carbamoyloxy; hydroxy(lower)alkyl (e.g., hydroxymethyl, 1 or 2-hydroxyethyl, 1 or 2 or 3-hydroxypropyl, etc.) or the like.

Suitable "hydroxy protective group" in the term "protected hydroxy" and "acyl having protected hydroxy" may include acyl as mentioned above, phenyl(lower)alkyl which may have one or more suitable substituent(s) (e.g., benzyl, 4-methoxybenzyl, trityl, etc.), trisubstituted silyl [e.g., tri (lower)alkylsilyl (e.g. trimethylsilyl, t-butyldimethylsilyl, etc.), etc.], tetrahydropyranyl and the like.

Suitable "aryl" and "aryl moiety" in the terms "ar(lower) alkyl", "ar(lower)alkenyl" and "ar($C_1$–$C_5$)alkyl" may include phenyl, naphthyl and the like.

Suitable "leaving group" and "leaving group moiety" in the term "acyl having a leaving group" may include acid residue and the like.

Suitable "acid residue" may include halogen (e.g., fluorine, chlorine, bromine, iodine), acyloxy [e.g., sulfonyloxy (e.g., phenylsulfonyloxy, tosyloxy, mesyloxy, etc.), lower alkanoyloxy (e.g., acetyloxy, propionyloxy, etc.), etc.] and the like.

Suitable "halogen" may include fluorine, bromine, chlorine, iodine.

Suitable "protected carboxy" and "protected carboxy moiety" in the term "protected carboxy(lower)alkyl" may include esterified carboxy and the like. And suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g., ethynyl ester, propynyl ester, etc.); lower alkoxy(lower)alkyl ester (e.g., methoxymethyl ester, ethoxymethyl ester, isopropoxy ester, 1-methoxyethyl ester, 1-ethoxyethyl ester, etc.); lower alkylthio(lower)alkyl ester (e.g., methylthiomethyl ester, ethylthiomethyl ester, ethylthioethyl ester, isopropoxythiomethyl ester, etc.); mono (or di or tri )halo (lower)alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 2-propionyloxyethyl ester, etc.); cyclo(lower)alkyl ester (e.g., cyclopropyl ester, cyclopentyl ester, cyclohexyl ester, etc.); lower alkoxycarbonyloxy (lower)alkyl ester (e.g., methoxycarbonyloxymethyl ester, ethoxycarbonyloxymethyl ester, propoxycarbonyloxymethyl ester, 1-(or 2-)[methoxycarbonyloxy]ethyl ester, 1-(or 2-)[ethoxycarbonyloxy]ethyl ester, 1-(or 2-)[propoxycarbonyloxy]ethyl ester, 1-(or 2-)[isopropoxycarbonyloxy]ethyl ester, etc.); lower alkanesulfonyl(lower)alkyl ester (e.g., mesylmethyl ester, 2-mesylethyl ester, etc.); lower alkoxycarbonyloxy(lower)alkyl ester (e.g., methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.); phthalidylidene (lower)alkyl ester, or(5-lower alkyl-2-oxo-1,3-dioxol-4-yl) (lower)alkyl ester [e.g., (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; ar(lower) alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-t-butylbenzyl ester, etc.); aryl ester which may have one or more suitable substituent(s)such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri (lower)alkyl silyl ester; lower alkylthioester (e.g., methylthioester, ethylthioester, etc.) and the like.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$-$C_4$ alkylene.

Suitable "heterocyclic group" can be referred to the ones as exemplified above.

Suitable "bridged tricyclicalkyl" may include tricyclobutyl, tricyclopentyl, tricyclohexyl, tricycloheptyl, tricyclooctyl, tricyclononanyl, tricyclodecanoyl (e.g., adamantanyl, etc.), tricycloundecanyl, and the like.

Suitable "cyclo(lower)alkyl" and "cyclo(lower)alkyl moiety" in the terms "cyclo(lower)alkyl-(lower)alkyl" and "cyclo(lower)alkyl-($C_1$-$C_5$)alkyl" may include cyclopropyl, cyclobutyl, cyclopentyl, cyclohexyl, and the like.

Suitable "$C_1$-$C_5$ alkyl" and "$C_1$-$C_5$ alkyl moiety" in the terms "cyclo(lower)alkyl-($C_1$-$C_5$)alkyl" and "ar($C_1$-$C_5$) alkyl" may include straight or branched one having 1 to 5 carbon atom(s), such as methyl, ethyl, propyl, isopropyl, butyl, isobutyl, sec-butyl, tert-butyl, pentyl, tert-pentyl, neopentyl, and the like.

Suitable "N-containing heterocyclic group" and "N-containing heterocyclic group moiety" in the term "acyl having N-containing heterocyclic group" may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, dihydropyridyl, triazolyl (e.g., 4H-1,2,4-triazolyl, 1H-1,2,3-triazolyl, 2H-1,2,3-triazolyl, etc.) tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, etc.;

saturated 3 to 8-membered (more preferably 5 or 6-membered) heteromonocyclic group containing 1 to 2 oxygen atom(s) and 1 to 3 nitrogen atom(s), for example, morpholinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.; and the like.

Suitable substituent" in the term" heterocyclic group which may have suitable substituent(s)" may include lower alkyl (e.g., methyl, ethyl, propyl, isopropyl, butyl, isobutyl, t-butyl, pentyl, neopentyl, t-pentyl, hexyl, etc.), lower alkoxy (e.g., methoxy, ethoxy, propoxy, isopropoxy, isobutoxy, t-butoxy, pentyloxy, neopentyloxy, t-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1-methylpropargyl, 1 or 2 or 3-butynyl, 1 or 2 or 3 or 4-pentynyl, 1 or 2 or 3 or 4 or 5-hexynyl, etc.), mono (or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine, iodine), carboxy, protected carboxy, hydroxy, protected hydroxy, aryl (e.g., phenyl, naphthyl, etc.), ar(lower)alkyl such as phenyl(lower) alkyl (e.g., benzyl, phenethyl, phenylpropyl, etc.), carboxy (lower)alkyl, protected carboxy(lower)alkyl, nitro, amino, protected amino, di(lower)alkylamino (e.g., dimethylamino, diethylamino, diisopropylamino, ethylmethylamino, isopropylmethylamino, ethylmethylamino, ethylpropylamino, etc.), hydroxy(lower)alkyl, protected hydroxy(lower)alkyl, acyl as mentioned above, cyano, mercapto, lower alkylthio (e.g., methylthio, ethylthio, propylthio, isopropylthio, butylthio, etc.), imino, and the like.

Suitable "substituent" in the term "aryl which may have suitable substituent", "ar(lower)alkyl which may have suitable substituent(s)" and "ar($C_1$-$C_5$)alkyl which may have suitable substituent(s)" may include lower alkyl (e.g., methyl, ethyl propyl, isopropyl, butyl, isobutyl, t-butyl, pentyl, neopentyl, t-pentyl, hexyl, etc.), lower alkoxy (e.g., methoxy, ethoxy, propoxy, isopropoxy, isobutoxy, t-butoxy, pentyloxy, neopentyloxy, t-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1-methylpropargyl, 1 or 2 or 3-butynyl, 1 or 2 or 3 or 4-pentynyl, 1 or 2 or 3 or 4 or 5-hexynyl, etc.), mono (or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine, iodine), carboxy, protected carboxy, hydroxy, protected hydroxy, aryl (e.g., phenyl, naphthyl, etc.), ar(lower)alkyl such as phenyl(lower)alkyl (e.g., benzyl, phenethyl, phenylpropyl, etc.), carboxy(lower)alkyl, protected carboxy(lower)alkyl, nitro, amino, protected amino, di(lower)alkylamino (e.g., dimethylamino, diethylamino, diisopropylamino, ethylmethylamino, isopropylmethylamino, ethylmethylamino, ethylpropylamino, etc.), hydroxy(lower)alkyl, protected hydroxy(lower)alkyl, acyl as mentioned above, cyano, mercapto, lower alkylthio (e.g., methylthio, ethylthio, propylthio, isopropylthio, butylthio, etc.), imino, and the like.

The processes for preparing the object and starting compounds are explained in detail in the following.

Process (1)

The compound (Ia) or a salt thereof can be prepared by subjecting the compound (II) or a salt thereof to reduction reaction.

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.);
a combination of borane, and tetrahydrofuran or di(lower)alkyl sulfide (e.g., dimethyl sulfide, etc.);
or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney copper, Ullman copper, etc.), and the like.

The reduction is usually carried out in a conventional solvent which does not adversely influence the reaction such as water, alcohol (e.g., methanol, ethanol, propanol, etc.), tetrahydrofuran, dioxane, N,N-dimethylformamide, or a mixture thereof.

Additionally, in case that the above-mentioned acids to be used in chemical reduction are in liquid, they can also be used as a solvent.

The reaction temperature is not critical and the reaction is usually carried out under cooling to warming.

Process (2)

The compound (Ic) or a salt thereof can be prepared by subjecting the compound (Ib) or its reactive derivative at the imino group or a salt thereof to acylation reaction.

Suitable acylating agent to be used in the present acylation reaction may include the compound of the formula:

$$R_a^4\text{—OH} \qquad (XIX)$$

(wherein $R_a^4$ is acyl) or its reactive derivative or a salt thereof.

Suitable reactive derivative at the imino group of the compound (Ib) may include a silyl derivative formed by the reaction of the compound (Ib) with a silyl compound such as N,O-bis(trimethylsilyl)acetamide, N-trimethylsilylacetamide or the like; a derivative formed by the reaction of the compound (Ib) with phosphorus trichloride or phosgene, and the like.

Suitable reactive derivative of the compound (XIX) may include an acid halide, an acid anhydride, an activated ester, isothiocyanate, isocyanate, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfuric acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl [(CH$_3$)$_2$N$^\oplus$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxyamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); substituted or unsubstituted aryl isocyanate; substituted or unsubstituted aryl isothiocyanate, and the like. These reactive derivatives can optionally be selected from them according to the kind of the compound (XIX) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (XIX) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole); pentamethyleneketene-N- cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may be carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri(lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine, lutidine, picoline, dimethylaminopyridine, N-(lower)alkylmorpholine, N,N-di(lower)alkylbenzylamine, N,N-di(lower)alkylamine, N-(lower)alkylpyrrolidone (e.g., N-methyl-2-pyrrolidone, etc.), or the like.

The reaction may be carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid, the base and/or the starting compound are in liquid, they can be used also as a solvent.

The reaction temperature is not critical and the reaction is usually carried out under cooling to heating.

The present invention includes, within the scope of the invention, the case that hydrogen in $R^3$ is transformed into acyl group during the reaction.

Process (3)

The compound (Ie) or a salt thereof can be prepared by subjecting the compound (Id) or a salt thereof to reduction reaction.

This reduction can be carried out in a similar manner to that of the aforementioned Process (1), and therefore the reagents to be used and the reaction conditions (e.g., solvent, reaction temperature, etc.) can be referred to those of the Process (1).

Process (4)

The compound (If) or a salt thereof can be prepared by subjecting the compound (III) or a salt thereof to reduction reaction.

This reduction can be carried out in a similar manner to that of the aforementioned Process (1), and therefore the reagents to be used solvent, reaction conditions (e.g., solvent, reaction temperature, etc.) can be referred to those of the Process (1).

Process (5)

The compound (Ih) or a salt thereof can be prepared by subjecting the compound (Ig) or a salt thereof to elimination reaction of the hydroxy protective group.

Suitable method of this elimination reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]-non-5-ene, or the like.

Suitable acid may include an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], or the like is preferably carried out in the presence of cation trapping agents [e.g., anisole, phenol, etc.].

The reaction is usually carried out in a conventional solvent such as water, alcohol (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

Among these solvents, hydrophilic solvents may be used in a mixture with water.

The reaction temperature is not critical and the reaction is usually carried out under cooling to warming.

(ii) For reduction:

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, etc.), and the like.

The reduction is usually carried out in a conventional solvent which does not adversely influence the reaction such as water, alcohol (e.g., methanol, ethanol, propanol, etc.), N,N-dimethylformamide, tetrahydrofuran, methylene dichloride, chloroform, dioxane, or a mixture thereof.

Additionally, in case that the above-mentioned acids to be used in chemical reduction are in liquid, they can also be used as a solvent.

The reaction temperature of this reduction is not critical and the reaction is usually carried out under cooling to warming.

Process (6)

The compound (Ij) or a salt thereof can be prepared by subjecting the compound (Ii) or a salt thereof to elimination reaction of the amino protective group.

This reaction can be carried out in a similar manner to that of the aforementioned Process (5), and therefore the reagents to be used and the reaction conditions (e.g., solvent, reaction temperature, etc.) can be referred to those of the Process (5).

Process (7)

The compound (il) or a salt thereof can be prepared by reacting the compound (Ik) or a salt thereof with the compound (IV) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under cooling to heating.

The reaction is usually carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri (lower)alkylamine (e.g., trimethylamine, triethylamine, diisopropylethylamine, etc.), alkali metal hydride (e.g., sodium hydride, etc.), alkali metal(lower)alkoxide (e.g. sodium methoxide, sodium ethoxide, etc.), pyridine, lutidine, picoline, dimethylaminopyridine, N-(lower) alkylmorpholine, N,N-di(lower)alkylbenzylamine, N,N-di (lower)alkylaniline or the like.

When the base and/or the starting compound are in liquid, they can be used also as a solvent.

Process (A)

The compound (VII) or a salt thereof can be prepared by reacting the compound (V) or a salt thereof with the compound (VI) or a salt thereof.

This reaction can be carried out in the manner disclosed in Preparation 2 or similar manners thereto.

Process (B)

The compound (IX) or a salt thereof can be prepared by reacting the compound (VII) or a salt thereof with the compound (VIII) or a salt thereof.

This reaction can be carried out in the manner disclosed in Preparation 3 or similar manners thereto.

Process (C)

The compound (X) or a salt thereof can be prepared by subjecting the compound (IX) or a salt thereof to cleavage reaction of O—N bond.

This reaction can be carried out in the manner disclosed in Preparation 4 or similar manners thereto.

Process (D)-①

The compound (XI) or a salt thereof can be prepared by subjecting the compound (X) or a salt thereof to halogenation reaction.

This halogenation is usually carried out by using a conventional halogenating agent such as halogen (e.g., chlorine, bromine, etc.), phosphorus trihalide (e.g., phosphorus tribromide, phosphorus trichloride, etc.), phosphorus pentahalide, (e.g., phosphorus pentachloride, phosphorus pentabromide, etc.), phosphorus oxychloride (e.g., phosphoryl trichloride, phosphoryl monochloride, etc.), thionyl halide (e.g., thionyl chloride, thionyl bromide, etc.), oxalyl halide (e.g., oxalyl chloride, oxalyl bromide, etc.) and the like.

This reaction is usually carried out in a solvent such as water, alcohol (e.g., methanol, ethanol, isopropyl alcohol, etc.), benzene, dioxane, N,N-dimethylformamide, tetrahydrofuran, methylene chloride, ethylene dichloride, chloroform, diethyl ether or any other solvent which does not adversely affect the reaction.

The reaction temperature is not critical and the reaction is usually carried out under cooling to warming.

Process (D)-②

The compound (XIII) or a salt thereof can be prepared by reacting the compound (XI) or a salt thereof with the compound (XII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under warming to heating.

Process (E)

The compound (X) or a salt thereof can be prepared by reacting the compound (XIV) or a salt thereof with the compound (XV) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate etc.), tri (lower)alkylamine (e.g., trimethylamine, triethylamine, diisopropylethylamine, etc.), alkali metal hydride (e.g., sodium hydride, etc.), alkali metal(lower)alkoxide (e.g., sodium methoxide, sodium ethoxide, etc.), pyridine, lutidine, picoline, dimethylaminopyridine, N-(lower) alkylmorpholine, N,N-di(lower)alkylbenzylamine, N,N-di (lower)alkylaniline or the like.

When the base and/or the starting compound are in liquid, they can be also as a solvent.

Process (F)

The compound (XIII) or a salt thereof can be prepared by reacting the compound (X) or a salt thereof with the compound (XII) or a salt thereof.

This reaction is usually carried out in a solvent such as benzene, N,N-dimethylformamide, tetrahydrofuran, toluene, methylene chloride, ethylene dichloride, chloroform, dioxane, diethyl ether or any other solvent which does not adversely affect the reaction.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be also as a solvent.

Process (G)

The compound (XVI) or a salt thereof can be prepared by subjecting the compound (XIII) or a salt thereof to diazotization reaction.

The reaction is usually carried out by using a conventional diazotizing agent such as a combination of an alkali metal nitrite (e.g., sodium nitrite, etc.) and an inorganic acid (e.g., hydrochloric acid, hydrobromic acid, nitric acid, sulfuric acid, etc.), a combination of isopentyl nitrite and an organic acid (e.g., acetic acid, benzoic acid, etc.) and the like.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under cooling.

Process (H)

The compound (IIa) or a salt thereof can be prepared by reacting the compound (XVI) or a salt thereof with the compound (XVII) or a salt thereof.

This reaction is usually carried out in a solvent such as water, alcohol (e.g, methanol, ethanol, etc.), benzene, N,N-dimethylformamide, tetrahydrofuran, toluene, methylenechloride, ethylene dichloride, chloroform, diethyl ether or any other solvent which does not adversely affect the reaction.

The reaction temperature is not critical and the reaction is usually carried out under cooling to warming.

Process (I)

The compound (II) or a salt thereof can be prepared by reacting the compound (Ib) or a salt thereof with the compound (XVIII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under cooling to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be used also as a solvent.

Suitable "anion" may include anion derived from the materials used in this reaction such as acid residue [e.g., halogen (e.g., fluorine, chlorine, bromine, iodine), etc.], OH⁻ and the like.

Suitable salts of the object and starting compounds in Process (1)–(7) and (A)–(I) can be referred to the ones as exemplified for the compound (I).

The new pyrazole derivatives(I) and a pharmaceutically acceptable salt thereof of the present invention possess a strong inhibitory activity on the production of Interleukin-1 (IL-1) and a strong inhibitory activity on the production of tumor necrosis factor (TNF), and therefore are useful as an inhibitor on the production of interleukin-1 (IL-1) and an inhibitor on the production of tumor necrosis factor (TNF).

Accordingly, the new pyrazole derivatives (I) and a pharmaceutically acceptable salt thereof can be used for prophylactic and therapeutic treatment of IL-1 and TNF mediated diseases such as chronic inflammatory diseases (e.g. rheumatoid arthritis, osteoarthritis, etc.) osteoporosis, rejection by transplantation, asthma, endotoxin shock, specific autoimmune diseases [e.g. ankylosing spondylitis, autoimmune hematological disorders (e.g. hemolyticodo anaemia, aplastic anaemia, pure red cell anaemia, idiopathic thrombocytopenia, etc.), systemic lupus erythematosus, polychondritis, scleroderma, Wegener granulamotosis, dermatomyositis, chronic active hepatitis, myasthenia gravis, psoriasis, idiopathic sprue, autoimmune inflammatory bowel disease (e.g. ulcerative colitis, Crohn's disease, etc.), endocrine opthalmopathy, Grave's disease, sarcoidosis, multiple scleosis, primary billiary cirrhosis, juvenile diabetes (diabetes mellitus type I), Reiter's syndrome, non infection uveitis, autoimmune keratitis (e.g. keratoconjuntivitis sicca, vernal keratoconjunctivitis, etc.), interstitial lung fibrosis, psoriatic arthritis, glomerulonephritis {e.g. nephrotic syndrome (e.g. idiopathic nephrotic syndrome, minimal change nephropathy, etc.), etc.}, etc.], cancer cachexia, AIDS cachexia, thrombosis, and the like.

In order to show the utilities of the pyrazole derivatives (I) and a pharmaceutically acceptable salt thereof of the present invention, pharmacological test data of the representative compounds of the pyrazole derivatives (I) are illustrated in the following.

The expression of each "Example 16- (5)" and Example 18-(2)in the following test means the compounds prepared in Example 16-(5) and Example 18-(2) respectively.

(a) Inhibitory activity on the production of Interleukin-1 (IL-1)

1. Test method

Purified human peripheral blood monocyte were stimulated with bacterial lipopolysaccharide (1 µg/$10^4$ cells) in the absence or presence of appropriately diluted test compound for 2 days at 37° C. in a humidified 5% $CO_2$ atmosphere. Culture supernatants were tested for IL-1 ELISA assay.

Test compound was dissolved in absolute DMSO (dimethyl sulfoxide) to achieve 10 mM stock solutions and was subsequently diluted in serum free RPMI1640.

IL-1 levels were quantified by a commercial ELISA kit (Ohtsuka assay, Japan) using a sandwich technique. The sensitivity levels for the detection of IL-1β were 20 pg/ml.

The inhibitory concentration that caused a 50% inhibition ($IC_{50}$) was calculated by regression analysis of the dose-response data.

2. Test result

| Test compound | $IC_{50}$ (M) |
| --- | --- |
| Example 16-(5) | $9.2 \times 10^{-8}$ |
| Example 18-(2) | $8.8 \times 10^{-8}$ |

(b) Inhibitory activity on the production of tumor necrosis factor (TNF)

1. Test method

Purified human peripheral blood monocyte were stimulated with bacterial lipopolysaccharide (1 µg/$10^4$ cells) in the absence or presence of appropriately diluted test compound for 2 days at 37° C. in a humidified 5% $CO_2$ atmosphere. Culture supernatants were tested for TNF ELISA assay.

TNF levels were quantified by a commercial ELISA kit (Endogen, Inc. USA) using a sandwich technique. The sensitivity levels for the detection of TNF were 12 pg/ml.

The inhibitory concentration that caused a 50% inhibition ($IC_{50}$) was calculated by regression analysis of the dose-response data.

2. Test result

| Test compound | IC$_{50}$ (M) |
|---|---|
| Example 16-(5) | $9.1 \times 10^{-8}$ |
| Example 18-(2) | $1.1 \times 10^{-7}$ |

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, ingestion, eye drops, etc. If needed, there may be included in the above preparation auxiliary substance such as stabilizing agent, wetting or emulsifying agent, buffer or any other commonly used additives.

The effective ingredient may usually be administered with a unit dose of 0.001 mg/kg to 500 mg/kg, preferably 0.01 mg/kg to 10 mg/kg, 1 to 4 times a day. However, the above dosage may be increased or decreased according to age, weight and conditions of the patient or the administering method.

Preferred embodiments of the object compound (I) are as follows.

$R^1$ is phenyl which may have 1 to 3 (more preferably one or two) suitable substituent(s) [more preferably phenyl which may have 1 to 3 (more preferably one or two; most preferably one) substituent(s) selected from the group consisting of lower alkyl, lower alkoxy, lower alkenyl, lower alkynyl, mono (or di or tri)halo(lower) alkyl, halogen, carboxy, protected carboxy, hydroxy, protected hydroxy, aryl, ar(lower)alkyl, carboxy (lower)alkyl, protected carboxy(lower)alkyl, amino, protected amino, di(lower)alkylamino, hydroxy(lower) alkyl, protected hydroxy(lower)alkyl, nitro, acyl, cyano, mercapto, lower alkylthio and imino; most preferably halophenyl]; or pyridyl which may have 1 to 3 (more preferably one or two) suitable substituent(s) [more preferably pyridyl which may have 1 to 3 (more preferably one or two; most preferably one) substituent (s) selected from the group consisting of lower alkyl, lower alkoxy, lower alkenyl, lower alkynyl, mono (or di or tri)halo(lower)alkyl, halogen, carboxy, protected carboxy, hydroxy, protected hydroxy, aryl, ar(lower) alkyl, carboxy(lower)alkyl, protected carboxy(lower) alkyl, amino, protected amino, di(lower)alkylamino, hydroxy(lower)alkyl, protected hydroxy(lower)alkyl, nitro, acyl, cyano, mercapto, lower alkylthio and imino; most preferably pyridyl], $R^2$ is phenyl which may have 1 to 3 (more preferably one or two) suitable substituent(s) (more preferably phenyl which may have 1 to 3 (more preferably one or two; most preferably one) substituent(s) selected from the group consisting of lower alkyl, lower alkoxy, lower alkenyl, lower alkynyl, mono (or di or tri)halo(lower) alkyl, halogen, carboxy, protected carboxy, hydroxy, protected hydroxy, aryl, ar(lower)alkyl, carboxy(lower) alkyl, protected carboxy(lower)alkyl, amino, protected amino, di(lower)alkylamino, hydroxy(lower)alkyl, protected hydroxy(lower)alkyl, nitro, acyl, cyano, mercapto, lower alkylthio and imino; most preferably halophenyl]; or pyridyl which may have 1 to 3 (more preferably one or two) suitable substituent(s) [more preferably pyridyl which may have 1 to 3 (more preferably one or two; most preferably one) substituent (s) selected from the group consisting of lower alkyl, lower alkoxy, lower alkenyl, lower alkynyl, mono (or di or tri)halo(lower)alkyl, halogen, carboxy, protected carboxy, hydroxy, protected hydroxy, aryl, ar(lower) alkyl, carboxy(lower)alkyl, protected carboxy(lower) alkyl, amino, protected amino, di(lower)alkylamino, hydroxy(lower)alkyl, protected hydroxy(lower)alkyl, nitro, acyl, cyano, mercapto, lower alkylthio and imino; most preferably pyridyl, halopyridyl or lower alkoxypyridyl], $R^3$ is hydrogen or lower alkanoyl, $R^4$ is hydrogen; lower alkyl; cyclo(lower)alkyl; cyclo (lower)alkyl-(lower)alkyl; carboxy(lower)alkyl; esterified carboxy(lower)alkyl [more preferably lower alkoxycarbonyl(lower)alkyl]; phenyl(lower)alkyl which may have 1 to 3 (more preferably one or two) suitable substituent(s) [more preferably phenyl(lower) alkyl which may have 1 to 3 (more preferably one or two) substituent(s) selected from the group consisting of halogen, lower alkyl, lower alkoxy, lower alkenyl, lower alkynyl, mono (or di or tri)halo(lower)alkyl and di(lower)alkylamino; most preferably mono (or di) halophenyl(lower)alkyl]; adamantanyl; phenyl(lower) alkenyl; tetrahydropyranyl, piperidyl or dioxaspiroundecanyl, each of which may have 1 to 3 (more preferably one or two) substituent(s) selected from the group consisting of lower alkyl and acyl [more preferably tetrahydropyranyl, piperidyl or dioxaspiroundecanyl, each of which may have one or two substituent(s) selected from the group consisting of lower alkyl and lower alkanoyl; most preferably tetrahydropyranyl, lower alkylpiperidyl, lower alkanoylpiperidyl, or di(lower) alkyldioxaspiroundecanyl]; indanyl; lower alkanoyl which may have 1 to 3 (more preferably one or two) suitable substituent(s) [more preferably lower alkanoyl which may have 1 to 3 (more preferably one or two; most preferably one) substituent(s) selected from the group consisting of carboxy, protected carboxy, lower alkoxy, halogen, protected amino, amino, hydroxy, protected hydroxy and di(lower)alkylamino; most preferably lower alkanoyl which may have a substituent selected from the group consisting of carboxy, esterified carboxy, lower alkoxy, halogen, lower alkoxycarbonylamino, lower alkanoylamino, amino, hydroxy, acyloxy (more preferably lower alkanoyloxy or cyclo(lower)alkylcarbonyloxy), and di(lower) alkylamino]; lower alkoxycarbonyl; lower alkoxyglyoxyloyl; lower alkylsulfonyl; cyclo(lower) alkylcarbonyl; aroyl which may have 1 to 3 (more preferably one or two) suitable substituent(s) [more preferably benzoyl which may have 1 to 3 (more preferably one or two) substituent(s) selected from the group consisting of mono (or di or tri)halo(lower)alkyl, halogen, protected hydroxy and hydroxy; most preferably benzoyl which may have one or two substituent(s) selected from the group consisting of trihalo(lower) alkyl, halogen, acyloxy (more preferably lower alkanoyloxy) and hydroxy]; ar(lower)alkanoyl which may have 1 to 3 (more preferably one or two) suitable substituent(s) [more preferably phenyl(lower)alkanoyl which may have 1 to 3 (more preferably one or two) substituent(s) selected from the group consisting of lower alkoxy, aryl, halogen and mono (or di or tri)halo (lower)alkyl; most preferably phenyl(lower)alkanoyl which may have one or two substituent(s) selected from the group consisting of lower alkoxy, phenyl, halogen and trihalo(lower)alkyl]; ar(lower)alkenoyl [more preferably phenyl(lower)alkenoyl]; arylthio(lower) alkanoyl [more preferably phenylthio(lower)alkanoyl]; arylcarbamoyl [more preferably phenylcarbamoyl]; aryl-thiocarbamoyl [more preferably phenyl-thiocarbamoyl]; arylglyoxyloyl which may have 1 to 3 (more preferably one or two) suitable substituent(s) [more preferably phenylglyoxyloyl which may have 1 to 3 (more preferably one or two; most preferably one) substituent(s) selected from the group consisting of mono(or di or tri)halo(lower)alkyl and lower alkoxy; most preferably phenylglyoxyloyl which may have a substituent selected from the group consisting of trihalo (lower)alkyl and lower alkoxy]; carbamoyl which may have one or two suitable substituent(s) selected from the group consisting of lower alkyl, hydroxy(lower) alkyl, protected hydroxy(lower)alkyl (more preferably acyloxy(lower)alkyl), lower alkoxy and cyclo(lower) alkyl; heterocycliccarbonyl [more preferably morpholinylcarbonyl]; heterocyclic(lower)alkanoyl [more preferably indolyl(lower)alkanoyl or morpholinyl(lower)alkanoyl]; or heterocycliccarbamoyl [more preferably piperidylcarbamoyl], and $R^5$ is hydrogen or lower alkyl.

The following Preparations and Examples are given for the purpose of illustrating the present invention in more detail.

Preparation 1

To a solution of 4-methylpyridine (74.4 g) and ethyl 4-fluorobenzoate (134.4 g) in dry tetrahydrofuran (600 ml) was added a 1.0M solution of lithium bis(trimethylsilyl) amide in tetrahydrofuran (1.6 l) dropwise with ice cooling. The mixture was stirred at ambient temperature for 30 minutes. To the reaction mixture was added hexane (2.2 l) and the separated solid was collected, washed with hexane and dried. The obtained solid was dissolved in 3N-hydrochloric acid (800 ml) and the solution was neutralized with an aqueous saturated sodium bicarbonate solution. The separated solid was collected, washed with water and dried to give 1-(4-fluorophenyl)-2-(pyridin-4-yl)ethan-1-one (148 g).

mp: 93°–94° C.

NMR (CDCl$_3$, δ): 4.28 (2H, s), 7.09–7.25 (4H, m), 8.01 (1H, d, J=5 Hz), 8.06 (1H, d, J=5 Hz), 8.60 (2H, d, J=6 Hz)

Preparation 2

A mixture of 1-(4-fluorophenyl)-2-(pyridin-4-yl)-ethan-1-one (5.12 g) and N,N-dimethylformamide dimethyl acetal (16 ml) was stirred at 100° C. for 3 hours under nitrogen. The cooled mixture was concentrated in vacuo. The residue was crystallized from isopropyl ether to yield 3-dimethylamino-1-(4-fluorophenyl)-2-(pyridin-4-yl)-2-propen-1-one (6.15 g).

NMR (CDCl$_3$,δ): 2.82 (6H, s), 6.99 (2H, t, J=9 Hz), 7.03 (2H, d, J=6 Hz), 7.35–7.55 (3H, m), 8.48 (2H, br)

Preparation 3

A mixture of 3-dimethylamino-1-(4-fluorophenyl)-2-(pyridin-4-yl)-2-propen-1-one (6.15 g) and hydroxylamine hydrochloride (4.75 g) in dry ethanol (40 ml) was refluxed for 20 minutes. The mixture was cooled and concentrated in vacuo. The residue was dissolved in dilute hydrochloric acid and then treated with an aqueous saturated sodium bicarbonate solution. The precipitates were collected by filtration, washed with water, and dried to give 5-(4-fluorophenyl)-4-(pyridin-4-yl)isoxazole (5.35 g).

mp: 95°–97° C.

NMR (CDCl$_3$, δ): 7.15 (2H, t, J=9 Hz), 7.37 (2H, d, J=6 Hz), 7.61 (2H, dd, J=5 Hz and 9 Hz), 8.46 (1H, s), 8.67 (2H, d, J=6 Hz)

Preparation 4

A suspension of 5-(4-fluorophenyl)-4-(pyridin-4-yl)-isoxazole (5.35 g) in 1N sodium hydroxide aqueous solution (50 ml) was stirred for one hour at 60° C. The solution was cooled and adjusted to pH 6 with concentrated hydrochloric acid. The separated solid was collected, washed with water, and dried to give 3-(4-fluorophenyl)-3-oxo-2-(pyridin-4-yl) propanenitrile (5.27 g).

mp: 222°–225° C.

NMR (CDCl$_3$+CD$_3$OD, δ): 7.11 (2H, t, J=9 Hz), 7.77 (2H, dd, J=5 Hz and 9 Hz), 7.82 (2H, d, J=6 Hz), 8.21 (2H, d, J=6 Hz)

Preparation 5

A solution of 3-(4-fluorophenyl)-3-oxo-2-(pyridin-4-yl) propanenitrile (240 mg) in phosphoryl trichloride (3 ml) was stirred for 15 minutes at 100° C. and then evaporated under reduced pressure. To the residue was added toluene and concentrated in vacuo, and the residue was dissolved in ethanol (2 ml). To the mixture was added hydrazine monohydrate (150 mg). The mixture was refluxed for 3 hours, cooled, and poured into an aqueous saturated sodium bicarbonate solution. The separated oil was extracted with a mixture of ethanol and dichloromethane (2:8). The extract was washed with water, dried and concentrated in vacuo. The residue was crystallized from methanol to yield 5-amino-3-(4-fluorophenyl)-4-(pyridin-4-yl)pyrazole (110 mg).

mp: >250° C.

NMR (CDCl$_3$+CD$_3$OD, δ): 7.08 (2H, t, J=9 Hz), 7.23 (2H, d, J=6 Hz), 7.33 (2H, dd, J=5 Hz and 9 Hz), 8.42 (2H, d, J=6 Hz)

Preparation 6

Sodium (2.48 g) was dissolved in dry ethanol (37 ml) under nitrogen atmosphere. To the solution was added 4-fluorophenylacetonitrile (11.65 g) and ethyl isonicotinate (16.41 ml) and the solution was refluxed for 3 hours. The reaction mixture was cooled and poured into water. The ethanol of the mixture was removed under reduced pressure. The resulting aqueous solution was washed with ether and neutralized with diluted hydrochloric acid. The separated solid was collected, washed with water and dried to give 2-(4-fluorophenyl)-3-oxo-3-(pyridin-4-yl)propanenitrile (16.43 g).

mp: 230°–232° C.

NMR (CDCl$_3$+CD$_3$OD, δ): 7.12 (2H, t, J=9 Hz), 7.68 (2H, d, J=6 Hz), 7.84 (2H, dd, J=5 Hz and 9 Hz), 8.69 (2H, d, J=6 Hz)

Preparation 7

A mixture of 2-(4-fluorophenyl)-3-oxo-3-(pyridin-4-yl) propanenitrile (10 g), hydrazine monohydrate (2.4 ml) and acetic acid (5.2 ml) in dry benzene (100 ml) was refluxed for 4 hours. The reaction mixture was cooled and extracted with 3N-hydrochloric acid (80 ml×3). The extracts were concentrated in vacuo to 100 ml of the volume and the solution was neutralized with aqueous ammonia solution. The separated solid was collected, washed with water and dried to give 5-amino-4-(4-fluorophenyl)-3-(pyridin-4-yl)pyrazole (2.02 g).

mp: 116°–118° C.

NMR (CDCl$_3$+CD$_3$OD, δ): 7.12 (2H, t, J=9 Hz), 7.25 (2H, dd, J=5 Hz and 9 Hz), 7.38 (2H, d, J=6 Hz), 8.46 (2H, d, J=6 Hz)

Preparation 8

To a mixture of 5-amino-4-(4-fluorophenyl)-3-(pyridin-4-yl)pyrazole (100 mg) and concentrated hydrochloric acid (0.2 ml) in water (0.4 ml) was added sodium nitrite (28 mg) in water (0.12 ml) under ice cooling. The mixture was stirred for 30 minutes and to the mixture were added cold dichloromethane (5 ml), an aqueous saturated sodium bicarbonate (2 ml) solution and 1-(triphenylphosphoranylidene)-2-propanone (126 mg) in dichloromethane (2 ml). The mixture was stirred at 10° C. for 2 hours. The organic layer was separated, dried and concentrated in vacuo. The residue was purified by column chromatography on silica gel and the obtained oil was crystallized from diisopropyl ether to give 8-(4-fluorophenyl)-4-methyl-7-(pyridin-4-yl)pyrazolo[5,1-c][1,2,4]triazine (41 mg).

mp: 202.5°–204.0° C.

NMR (CDCl$_3$, δ): 2.91 (3H, s), 7.18 (2H, t, J=9 Hz), 7.62 (2H, dd, J=5 Hz and 9 Hz), 7.68 (2H, d, J=6 Hz), 8.70 (2H, d, J=6 Hz), 8.79 (1H, s)

Preparation 9

The following compounds were obtained according to a similar manner to that of Preparation 8.

(1) 8-(4-Fluorophenyl)-7-(pyridin-4-yl)pyrazolo[5,1-c][1,2,4]triazine mp : 180°–182° C.

NMR (CDCl$_3$, δ): 7.20 (2H, t, J=9 Hz), 7.55–7.70 (4H, m), 8.59 (1H, d, J=5 Hz), 8.70 (2H, d, J=6 Hz), 8.90 (1H, d, J=5 Hz)

(2) 7-(4-Fluorophenyl)-4-methyl-8-(pyridin-4-yl)pyrazolo[5,1-c][1,2,4]triazine mp : 220°–223° C. (dec.)

NMR (CDCl$_3$, δ): 2.90 (3H, s), 7.17 (2H, t, J=9 Hz), 7.60–7.75 (4H, m), 8.67 (2H, d, J=6 Hz), 8.81 (1H, m)

(3) 7-(4-Fluorophenyl)-8-(pyridin-4-yl)pyrazolo[5,1-c][1,2,4]triazine

NMR (CDCl$_3$, δ): 7.18 (2H, t, J=9 Hz), 7.60–7.75 (4H, m), 8.59 (1H, d, J=4 Hz), 8.68 (2H, d, J=6 Hz), 8.93 (1H, d, J=4 Hz)

Preparation 10

The following compounds were obtained according to a similar manner to that of Preparation 1.

2-(2-Chloropyridin-4-yl)-1-(4-fluorophenyl)ethan-1-one mp: 99°–103° C.

NMR (CDCl$_3$, δ): 4.28 (2H, s), 7.11–7.22 (3H, m), 7.27 (1H, s), 8.03 (2H, dd, J=6 Hz and 9 Hz), 8.37 (1H, d, J=6 Hz)

(2) 2-(2-Bromopyridin-4-yl)-1-(4-fluorophenyl)ethan-1-one mp: 100°–104° C.

NMR (CDCl$_3$, δ): 4.25 (2H, s), 7.14–7.24 (3H, m), 7.40 (1H, s), 8.02 (2H, dd, J=6 Hz and 9 Hz), 8.35 (1H, d, J=6 Hz)

Preparation 11

The following compounds were obtained according to similar manners to those of Preparation 2 and 3.

(1) 4-(2-Chloropyridin-4-yl)-5-(4-fluorophenyl)isoxazole mp: 94°–96° C.

NMR (CDCl$_3$, δ): 7.17 (2H, t, J=9 Hz), 7.22 (1H, d, J=6 Hz), 7.36 (1H, s), 7.62 (2H, dd, J=6 Hz and 9 Hz), 8.41 (1H, d, J=6 Hz), 8.43 (1H, s)

(2) 4-(2-Bromopyridin-4-yl)-5-(4-fluorophenyl)isoxazole mp: 136°–138° C.

NMR (CDCl$_3$, δ): 7.28 (2H, t, J=9 Hz), 7.24 (1H, d, J=6 Hz), 7.53 (1H, s), 7.63 (2H, dd, J=6 Hz and 9 Hz), 8.39 (1H, d, J=6 Hz), 8.44 (1H, s)

Preparation 12

The following compounds were obtained according to similar manners to those of Preparation 4 and 6.

(1) 2-(2-Chloropyridin-4-yl)-3-(4-fluorophenyl)-3-oxopropanenitrile mp: 204°–206° C. (dec.)

NMR (CDCl$_3$+CD$_3$OD, δ): 7.13 (2H, t, J=9 Hz), 7.72 (2H, dd, J=6 Hz and 9 Hz), 7.78–7.90 (2H, m), 8.08 (1H, m)

(2) 2-(2-Bromopyridin-4-yl)-3-(4-fluorophenyl)-3-oxopropanenitrile mp: 217°–219° C. (dec.)

NMR (CDCl$_3$+CD$_3$OD, δ): 7.13 (2H, t, J=9 Hz), 7.73 (2H, dd, J=6 Hz and 9 Hz), 7.79–7.90 (2H, m), 8.23 (1H, m)

Preparation 13

The following compounds were obtained according to similar manners to those of Preparation 5 and 7.

(1) 5-Amino-4-(2-chloropyridin-4-yl)-3-(4-fluorophenyl)pyrazole mp: 213°–216° C.

NMR (CDCl$_3$+CD$_3$OD, δ): 7.03–7.14 (3H, m), 7.29–7.38 (3H, m), 8.23 (1H, d, J=6 Hz)

(2) 5-Amino-4-(2-bromopyridin-4-yl)-3-(4-fluorophenyl)pyrazole mp: 213°–215° C.

NMR (CDCl$_3$+CD$_3$OD, δ): 7.01–7.14 (3H, m), 7.28–7.47 (3H, m), 8.24 (1H, d, J=6 Hz)

Preparation 14

The following compounds were obtained according to a similar manner to that of Preparation 8.

(1) 8-(2-Chloropyridin-4-yl)-7-(4-fluorophenyl)pyrazolo[5,1-c][1,2,4]triazine mp: >250° C.

NMR (DMSO-d$_6$, δ): 7.40 (2H, t, J=9 Hz), 7.58 (1H, d, J=6 Hz), 7.70 (2H, dd, J=6 Hz and 9 Hz), 7.80 (1H, s), 8.49 (1H, d, J=6 Hz), 9.20 (1H, d, J=5 Hz), 9.40 (1H, d, J=5 Hz)

(2) 8-(2-Bromopyridin-4-yl)-7-(4-fluorophenyl)pyrazolo[5,1-c][1,2,4]triazine mp: 258° C. (dec.)

NMR (DMSO-d$_6$, δ): 7.42 (2H, t, J=9 Hz), 7.58 (1H, d, J=6 Hz), 7.71 (2H, dd, J=6 Hz and 9 Hz), 7.80 (1H, s), 8.50 (1H, d, J=6 Hz), 9.20 (1H, d, J=5 Hz), 9.43 (1H, d, J=5 Hz)

(3) 7-(4-Fluorophenyl)-8-(2-fluoropyridin-4-yl)pyrazolo[5,1-c][1,2,4]triazine mp: 240°–242° C.

NMR (CDCl$_3$:CD$_3$OD=9:1, δ): 7.23 (2H, t, J=9 Hz), 7.42 (1H, s), 7.57 (1H, d, J=6 Hz), 7.69 (2H, dd, J=6 Hz and 9 Hz), 8.24 (1H, d, J=6 Hz), 8.78 (1H, d, J=4 Hz), 9.01 (1H, d, J=4 Hz)

Preparation 15

To a suspension of 7-(4-fluorophenyl)-8-(2-fluoropyridin-4-yl)pyrazolo[5,1-c][1,2,4]triazine (350 mg) in methanol (2 ml) was added conc. sulfuric acid (0.32 ml) dropwise. The mixture was refluxed for 1 hour, cooled and poured into cold water. The aqueous solution was neutralized with an aqueous saturated sodium bicarbonate solution and the separated oil was extracted with dichloromethane. The extract was washed with brine, dried and concentrated in vacuo. The residue was purified by column chromatography on silica gel and the obtained oil was crystallized from methanol to give 7-(4-fluorophenyl)-8-(2-methoxypyridin-4-yl)pyrazolo[5,1-c][1,2,4]triazine (220 mg).

mp: 223°–225° C.

NMR (CDCl$_3$:CD$_3$OD=9:1, δ): 3.99 (3H, s), 7.10–7.25 (4H, m), 7.69 (2H, dd, J=6 Hz and 9 Hz), 8.21 (1H, d, J=6 Hz), 8.68 (1H, d, J=4 Hz), 8.93 (1H, d, J=4 Hz)

EXAMPLE 1

To a suspension of 7-(4-fluorophenyl)-8-(pyridin-4-yl)pyrazolo[5,1-c][1,2,4]triazine (2.2 g) in methanol (20 ml) was added sodium cyanoborohydride (480 mg). The pH of the mixture was maintained at 3 to 4 for 2 hours with 1N hydrochloric acid. The procedure was repeated three additional times to completely finish the reduction. Then, the mixture was concentrated in vacuo and the residue was dissolved in 2N hydrochloric acid. The mixture was stirred at 80° C. for 30 minutes and cooled. The solution was neutralized with an aqueous saturated sodium bicarbonate solution. The separated solid was collected, washed with water and methanol and dried to give 7-(4-fluorophenyl)-8-(pyridin-4-yl)-1,2,3,4-tetrahydropyrazolo[5,1-c][1,2,4]triazine (2.06 g).

mp: 233°–235° C.

NMR (CDCl$_3$:CD$_3$OD=9:1, δ): 3.37 (2H, t, J=6 Hz), 4.17 (2H, t, J=6 Hz), 7.13 (2H, t, J=9 Hz), 7.30–7.50 (4H, m), 8.24 (2H, d, J=6 Hz)

EXAMPLE 2

The following compounds were obtained according to a similar manner to that of Example 1.
(1) 7-(4-Fluorophenyl)-4-methyl-8-(pyridin-4-yl)-1,2,3,4-tetrahydropyrazolo[5,1-c][1,2,4]triazine mp: 219°–221° C.

NMR (CDCl$_3$:CD$_3$OD=9:1, δ): 1.60 (3H, d, J=7 Hz), 3.05 (1H, dd, J=6 Hz and 14 Hz), 3.38 (1H, dd, J=4 Hz and 14 Hz), 4.33 (1H, m), 7.06 (2H, t, J=9 Hz), 7.12 (2H, d, J=6 Hz), 7.40 (2H, dd, J=6 Hz and 9 Hz), 8.37 (2H, d, J=6 Hz)
(2) 8-(4-Fluorophenyl)-7-(pyridin-4-yl)-1,2,3,4-tetrahydropyrazolo[5,1-c][1,2,4]triazine mp: >250° C.

NMR (CDCl$_3$, δ): 3.38 (2H, q, J=6 Hz), 3.60 (1H, m), 4.21 (2H, t, J=6 Hz), 5.47 (1H, d, J=5 Hz), 7.06 (2H, t, J=9 Hz), 7.19 (2H, dd, J=6 Hz and 9 Hz), 7.35 (2H, d, J=6 Hz), 8.49 (2H, d, J=6 Hz)

EXAMPLE 3

To a solution of 7-(4-fluorophenyl)-8-(pyridin-4-yl)-1,2,3,4-tetrahydropyrazolo[5,1-c][1,2,4]triazine (207 mg) in acetic acid (2 ml) was added acetic anhydride (75 mg) with ice cooling. The solution was stirred at ambient temperature for 1 hour and concentrated in vacuo. The residue was dissolved in water (3 ml) and the solution was neutralized with an aqueous saturated sodium bicarbonate solution. The separated oil was extracted with dichloromethane and the extract was dried and concentrated in vacuo. The residue was crystallized from ethyl acetate to give 2-acetyl-7-(4-fluorophenyl)-8-(pyridin-4-yl)-1,2,3,4-tetrahydropyrazolo[5,1-c][1,2,4]triazine (195 mg).

mp: 216°–218° C.

NMR (CDCl$_3$:CD$_3$OD=9:1, δ): 2.28 (3H, s), 4.13 (2H, t, J=6 Hz), 4.26 (2H, t, J=6 Hz), 7.05 (2H, t, J=9 Hz), 7.27 (2H, d, J=6 Hz), 7.40 (2H, dd, J=6 Hz and 9 Hz), 8.42 (2H, d, J=6 Hz)

EXAMPLE 4

The following compounds were obtained according to a similar manner to that of Example 3.
(1) 2-Acetyl-8-(4-fluorophenyl)-7-(pyridin-4-yl)-1,2,3,4-tetrahydropyrazolo[5,1-c][1,2,4]triazine mp: 115°–120° C.

NMR (CDCl$_3$, δ): 2.28 (3H, s), 4.14 (2H, t, J=6 Hz), 4.28 (2H, t, J=6 Hz), 6.08 (1H, s), 7.09 (2H, t, J=9 Hz), 7.23 (2H, dd, J=6 Hz and 9 Hz), 7.35 (2H, d, J=6 Hz), 8.49 (2H, d, J=6 Hz)
(2) 7-(4-Fluorophenyl)-2-formyl-8-(pyridin-4-yl)-1,2,3,4-tetrahydropyrazolo[5,1-c][1,2,4]triazine mp: 233°–235° C.

NMR (CDCl$_3$, δ): 4.10–4.20 (2H, m), 4.25–4.40 (2H, m), 6.50 (1H, br s), 7.05 (2H, t, J=9 Hz), 7.15 (2H, d, J=6 Hz), 7.40 (2H, dd, J=6 Hz and 9 Hz), 8.45 (2H, d, J=6 Hz), 8.55 (1H, s)

EXAMPLE 5

To a mixture of 7-(4-fluorophenyl)-8-(pyridin-4-yl)-1,2,3,4-tetrahydropyrazolo[5,1-c][1,2,4]triazine (148 mg) and triethylamine (101 mg) in dry dichloromethane was added acetic anhydride (54 mg). The reaction mixture was stirred at ambient temperature for 4 hours and then, to the mixture was added methanol (1 ml). After standing for 30 minutes, the mixture was concentrated in vacuo. The residue was purified by column chromatography on silica gel. The first fraction was concentrated in vacuo and the obtained oil was crystallized from a mixture of diethyl ether and n-hexane to give 1,2-diacetyl-7-(4-fluorophenyl)-8-(pyridin-4-yl)-1,2,3,4-tetrahydropyrazolo-[5,1-c][1,2,4]triazine (22 mg).

mp: 162°–164° C.

NMR (CDCl$_3$, δ): 2.11 (3H, s), 2.32 (3H, s), 3.40 (1H, m), 4.20–4.45 (2H, m), 5.07 (1H, dd, J=6 Hz and 14 Hz), 7.10 (2H, t, J=9 Hz), 7.14 (2H, d, J=6 Hz), 7.33 (2H, dd, J=6 Hz and 9 Hz), 8.58 (2H, d, J=6 Hz)

The second fraction was concentrated in vacuo and the obtained oil was crystallized from ethyl acetate to give 2-acetyl-7-(4-fluorophenyl)-8-(pyridin-4-yl)-1,2,3,4-tetrahydropyrazolo[5,1-c][1,2,4]triazine (101 mg).

mp: 216°–218° C.

NMR (CDCl$_3$:CD$_3$OD=9:1, δ): 2.28 (3H, s), 4.12 (2H, t, J=6 Hz), 4.25 (2H, t, J=6 Hz), 7.07 (2H, t, J=9 Hz), 7.20 (2H, d, J=6 Hz), 7.40 (2H, dd, J=6 Hz and 9 Hz), 8.42 (2H, d, J=6 Hz)

EXAMPLE 6

The following two compounds were obtained by reacting 7-(4-fluorophenyl)-4-methyl-8-(pyridin-4-yl)-1,2,3,4-tetrahydro[5,1-c][1,2,4]triazine according to a similar manner to that of Example 5.

2-Acetyl-7-(4-fluorophenyl)-4-methyl-8-(pyridin-4-yl)-1,2,3,4-tetrahydropyrazolo[5,1-c][1,2,4]triazine mp: 247°–249° C.

NMR (CDCl$_3$:CD$_3$OD=9:1, δ): 1.60 (3H, d, J=7 Hz), 2.30 (3H, s), 3.93 (1H, dd, J=6 Hz and 13 Hz), 4.10 (1H, dd, J=5 Hz and 13 Hz), 4.46 (1H, m), 7.06 (2H, t, J=9 Hz), 7.21 (2H, d, J=6 Hz), 7.41 (2H, dd, J=6 Hz and 9 Hz), 8.42 (2H, d, J=6 Hz)

1,2-Diacetyl-7-(4-fluorophenyl)-4-methyl-8-(pyridin-4-yl)-1,2,3,4-tetrahydropyrazolo[5,1-c][1,2,4]triazine mp: 193°–194° C.

NMR (CDCl$_3$, δ): 1.71 (3H, d, J=7 Hz), 2.12 (3H, s), 2.31 (3H, s), 3.00 (1H, dd, J=11 Hz and 13 Hz), 4.43 (1H, m), 5.05 (1H, dd, J=6 Hz and 13 Hz), 7.00 (2H, t, J=9 Hz), 7.13 (2H, d, J=6 Hz), 7.35 (2H, dd, J=6 Hz and 9 Hz), 8.58 (2H, d, J=6 Hz)

EXAMPLE 7

To a mixture of 7-(4-fluorophenyl)-8-(pyridin-4-yl)-1,2,3,4-tetrahydropyrazolo[5,1-c][1,2,4]triazine (100 mg, 0.339 mmol) and pyridine (54 mg, 0.678 mmol) in N-methyl-2-pyrrolidone (1.5 ml) was added acetoxyacetyl chloride (60 mg, 0.441 mmol) in N-methyl-2-pyrrolidone (0.5 ml) under nitrogen atmosphere with ice cooling. After stirring for 30 minutes, the reaction mixture was diluted with an aqueous saturated sodium bicarbonate solution, then extracted with ethyl acetate. The organic phase was washed with water and brine, dried over sodium sulfate, and concentrated in vacuo. The residue was purified by chromatography on silica gel (eluent:dichloromethane/methanol; 100/1~20/1) and the obtained amorphous product was crystallized from diisopropyl ether to give 2-acetoxyacetyl-7-(4-fluorophenyl)-8-(pyridin-4-yl)-1,2,3,4-tetrahydropyrazolo-[5,1-c][1,2,4]triazine (76 mg).

mp: 121° C. (dec.)

NMR (DMSO-d$_6$, δ): 2.10 (3H, s), 3.95–4.05 (2H, m), 4.10–4.20 (2H, m), 4.90 (2H, s), 7.15–7.30 (4H, m), 7.35–7.45 (2H, m), 8.45 (2H, d, J=6 Hz), 8.70 (1H, s)

EXAMPLE 8

The following compounds were obtained according to a similar manner to that of Example 7.

(1) 7-(4-Fluorophenyl)-2-methylsulfonyl-8-1pyridin-4-yl)-1,2,3,4-tetrahydropyrazolo[5,1-c][1,2,4]triazine mp: 133°–135° C.

NMR (CDCl$_3$:CD$_3$OD=9:1, δ): 3.16 (3H, s), 4.03 (2H, t, J=6 Hz), 4.33 (2H, t, J=6 Hz), 7.08 (2H, t, J=9 Hz), 7.30–7.45 (4H, m), 8.40 (2H, d, J=6 Hz)

(2) 7-(4-Fluorophenyl)-2-methoxycarbonyl-8-(pyridin-4-yl)-1,2,3,4-tetrahydropyrazolo[5,1-c][1,2,4]triazine mp: 215°–216° C.

NMR (DMSO-d$_6$, δ): 3.65 (3H, s), 3.90–4.00 (2H, m), 4.10–4.25 (2H, m), 7.15 (2H, d, J=6 Hz), 7.20 (2H, t, J=9 Hz), 7.40 (2H, dd, J=6 Hz and 9 Hz), 8.45 (2H, d, J=6 Hz), 8.55 (1H, s)

(3) 7-(4-Fluorophenyl)-8-(pyridin-4-yl)-2-[4-(trifluoromethyl)benzoyl]-1,2,3,4-tetrahydropyrazolo[5,1-c][1,2,4]triazine mp: 207°–209° C.

NMR (DMSO-d$_6$, δ): 4.10–4.40 (4H, m), 6.75–6.90 (2H, m), 7.10–7.45 (4H, m), 7.75–7.85 (4H, m), 8.20–8.35 (2H, m)

(4) 2-Cinnamoyl-7-(4-fluorophenyl)-8-(pyridin-4-yl)-1,2,3,4-tetrahydropyrazolo[5,1-c][1,2,4]triazine mp: 228°–230° C.

NMR (CDCl$_3$, δ): 4.25–4.40 (4H, m), 6.25 (1H, br s), 7.05 (2H, t, J=9 Hz), 7.20 (2H, d, J=6 Hz), 7.30–7.60 (8H, m), 7.80 (1H, d, J=15 Hz), 8.55 (2H, d, J=6 Hz)

(5) 2-Benzoyl-7-(4-fluorophenyl)-8-(pyridin-4-yl)-1,2,3,4-tetrahydropyrazolo[5,1-c][1,2,4]triazine mp: 141° C. (dec.)

NMR (CDCl$_3$, δ): 4.20–4.40 (4H, m), 6.85–7.10 (4H, m), 7.40 (2H, dd, J=6 Hz and 9 Hz), 7.45–7.65 (5H, m), 8.30–8.45 (2H, m)

(6) 2-[4-(Acetoxy)benzoyl]-7-(4-fluorophenyl)-8-(pyridin-4-yl)-1,2,3,4-tetrahydropyrazolo[5,1-c][1,2,4]triazine mp: 148° C. (dec.)

NMR (CDCl$_3$, δ): 2.35 (3H, s), 4.25–4.40 (4H, m), 6.90–7.10 (4H, m), 7.20 (2H, t, J=9 Hz), 7.40 (2H, dd, J=6 Hz and 9 Hz), 7.65 (2H, d, J=9 Hz), 8.40 (2H, d, J=6 Hz)

(7) 2-(3-Carboxypropanoyl)-7-(4-fluorophenyl)-8-(pyridin-4-yl)-1,2,3,4-tetrahydropyrazolo[5,1-c][1,2,4]triazine mp: 214°–215° C.

NMR (DMSO-d$_6$, δ): 2.45 (2H, t, J=6 Hz), 2.72 (2H, t, J=6 Hz), 4.02 (2H, t, J=5 Hz), 4.15 (2H, t, J=5 Hz), 7.10–7.30 (4H, m), 7.40 (2H, dd, J=6 Hz and 9 Hz), 8.49 (2H, d, J=6 Hz), 8.70 (1H, s)

(8) 2-Chloroacetyl-7-(4-fluorophenyl)-8-(pyridin-4-yl)-1,2,3,4-tetrahydropyrazolo[5,1-c][1,2,4]triazine NMR (CDCl$_3$, δ): 4.15–4.25 (2H, m), 4.25–4.35 (2H, m), 4.40 (2H, s), 6.45 (1H, s), 7.00 (2H, t, J=9 Hz), 7.15 (2H, d, J=6 Hz), 7.40 (2H, dd, J=6 Hz and 9 Hz), 8.50 (2H, d, J=6 Hz)

(9) 7-(4-Fluorophenyl)-2-methoxyacetyl-8-(pyridin-4-yl)-1,2,3,4-tetrahydropyrazolo[5,1-c][1,2,4]triazine mp: 219° C. (dec.)

NMR (CDCl$_3$, δ): 3.45 (3H, s), 4.10–4.25 (2H, m), 4.25–4.35 (2H, m), 4.40 (2H, s), 6.45 (1H, br s), 7.05 (2H, t, J=9 Hz), 7.15 (2H, d, J=6 Hz), 7.40 (2H, dd, J=6 Hz and 9 Hz), 8.50 (2H, d, J=6 Hz)

(10) 7-(4-Fluorophenyl)-2-pivaloyl-8-(pyridin-4-yl)-1,2,3,4-tetrahydropyrazolo[5,1-c][1,2,4]triazine mp: 248°–250° C.

NMR (CDCl$_3$, δ): 1.30 (9H, s), 4.10–4.20 (2H, m), 4.22–4.32 (2H, m), 6.28 (1H, br s), 7.04 (2H, t, J=9 Hz), 7.14 (2H, d, J=6 Hz), 7.41 (2H, dd, J=6 Hz and 9 Hz), 8.50 (2H, d, J=6 Hz)

(11) 2-Cyclohexylcarbonyl-7-(4-fluorophenyl)-8-(pyridin-4-yl)-1,2,3,4-tetrahydropyrazolo[5,1-c][1,2,4]triazine mp: 209°–211° C.

NMR (CDCl$_3$, δ): 1.20–1.60 (6H, m), 1.70–1.90 (4H, m), 2.95–3.10 (1H, m), 4.10–4.30 (4H, m), 6.15 (1H, br s), 7.05 (2H, t, J=9 Hz), 7.15 (2H, d, J=6 Hz), 7.40 (2H, dd, J=6 Hz and 9 Hz), 8.50 (2H, d, J=6 Hz)

(12) 2-Cyclohexylcarbonyloxyacetyl-7-(4-fluorophenyl)-8-(pyridin-4-yl)-1,2,3,4-tetrahydropyrazolo[5,1-c][1,2,4]triazine mp: 178°–181° C.

NMR (CDCl$_3$, δ): 1.20–1.83 (8H, m), 1.90–2.05 (2H, m), 2.35–2.52 (1H, m), 4.10–4.20 (2H, m), 4.24–4.35 (2H, m), 5.00 (2H, s), 6.54 (1H, s), 7.05 (2H, t, J=9 Hz), 7.12 (2H, d, J=6 Hz), 7.40 (2H, dd, J=6 Hz and 9 Hz), 8.50 (2H, d, J=6 Hz)

(13) 2-Cyclopropylcarbonyl-7-(4-fluorophenyl)-8-(pyridin-4-yl)-1,2,3,4-tetrahydropyrazolo[5,1-c][1,2,4]triazine mp: 192°–194° C.

NMR (CDCl$_3$, δ): 0.80–1.15 (4H, m), 2.52 (1H, m), 4.10–4.35 (4H, m), 6.52 (1H, s), 7.04 (2H, t, J=9 Hz), 7.17 (2H, d, J=6 Hz), 7.40 (2H, dd, J=6 Hz and 9 Hz), 8.49 (2H, d, J=6 Hz)

(14) 2-(3,3-Dimethylbutyryl)-7-(4-fluorophenyl)-8-(pyridin-4-yl)-1,2,3,4-tetrahydropyrazolo[5,1-c][1,2,4]triazine mp: 120° C. (dec.)

NMR (CDCl$_3$, δ): 1.03 (9H, s), 2.60 (2H, s), 4.14–4.30 (4H, m), 6.08 (1H, s), 7.03 (2H, t, J=9 Hz ), 7.17 (2H, d, J=6 Hz), 7.40 (2H, dd, J=6 Hz and 9 Hz), 8.50 (2H, d, J=6 Hz)

(15) 7-(4-Fluorophenyl)-2-isopropyloxycarbonyl-8-(pyridin- 4-yl)-1,2,3,4-tetrahydropyrazolo[5,1-c][1,2,4]triazine mp: 170°–172° C.

NMR (CDCl$_3$, δ): 1.32 (6H, d, J=6 Hz), 4.10 (2H, t, J=5 Hz), 4.25 (2H, t, J=5 Hz), 5.01 (1H, quint, J=6 Hz), 6.60 (1H, br s), 7.03 (2H, t, J=9 Hz), 7.16 (2H, d, J=6 Hz), 7.40 (2H, dd, J=6 Hz and 9 Hz), 8.51 (2H, d, J=6 Hz)

(16) 2-(3-Chloro-2,2-dimethylpropionyl)-7-(4-fluorophenyl)-8-(pyridin-4-yl)-1,2,3,4-tetrahydropyrazolo[5,1-c][1,2,4]triazine mp: 188°–189° C.

NMR (CDCl$_3$, δ): 1.20 (6H, s), 3.20 (2H, s), 4.14 (2H, t, J=5.5 Hz), 4.32 (2H, t, J=5.5 Hz), 7.00 (2H, t, J=9 Hz), 7.18 (2H, d, J=6 Hz), 7.30 (2H, dd, J=6 Hz and 9 Hz), 8.58 (2H, d, j=6 Hz)

(17) 2-(2,2-Dimethylbutyryl)-7-(4-fluorophenyl)-8-(pyridin-4-yl)-1,2,3,4-tetrahydropyrazolo[5,1-c][1,2,4]triazine mp: 204° C. (dec.)

NMR (CDCl$_3$, δ): 0.79 (3H, t, J=9 Hz), 1.27 (6H, s), 1.70 (2H, q, J=9 Hz), 4.12–4.21 (2H, m), 4.24–4.33 (2H, m), 6.20 (1H, br s), 7.04 (2H, t, J=9 Hz), 7.13 (2H, d, J=6 Hz), 7.43 (2H, dd, J=6 Hz and 9 Hz), 8.52 (2H, d, J=6 Hz)

(18) 2-Ethoxalyl-7-(4-fluorophenyl)-8-(pyridin-4-yl)-1,2,3,4-tetrahydropyrazolo[5,1-c][1,2,4]triazine mp: 174°–176° C.

NMR (CDCl$_3$, δ): 1.29 (3H, t, J=7 Hz), 4.18 (2H, t, J=6 Hz), 4.25–4.45 (4H, m), 6.95–7.15 (4H, m), 7.39 (2H, dd, J=6 Hz and 9 Hz), 8.37 (2H, d, J=6 Hz)

(19) 7-(4-Fluorophenyl)-2-[(3-methoxyphenyl)glyoxyloyl]-8-(pyridin-4-yl)-1,2,3,4-tetrahydropyrazolo[5,1-c][1,2,4]triazine hydrochloride mp: 270°–179° C. (dec.)

NMR (CDCl$_3$, +CD$_3$OD, δ): 3.80 (3H, s), 4.30–4.40 (2H, m), 4.40–4.50 (2H, m), 7.07–7.19 (3H, m), 7.25–7.40 (7H, m), 8.22 (2H, d, J=6 Hz)

(20) 2-Acetoxyacetyl-8-(4-fluorophenyl)-7-(pyridin-4-yl)-1,2,3,4-tetrahydropyrazolo[5,1-c][1,2,4]triazine mp: 231°–232° C.

NMR (CDCl$_3$:CD$_3$OD=9:1δ): 2.18 (3H, s), 4.13 (2H, t, J=6 Hz), 4.30 (2H, t, J=6 Hz), 4.92 (2H, s), 7.09 (2H, t, J=9 Hz), 7.21 (2H, dd, J=6 Hz and 9 Hz), 7.36 (2H, d, J=6 Hz), 8.48 (2H, d, J=6 Hz)

EXAMPLE 9

A mixture of 7-(4-fluorophenyl)-8-(pyridin-4-yl)-1,2,3,4-tetrahydropyrazolo[5,1-c][1,2,4]triazine (118 mg) and ethyl isocyanate (30 mg) in dichloromethane (2 ml) was stirred at ambient temperature for 1 hour. The mixture was concentrated in vacuo and the residue was crystallized from ethyl acetate to give 2-ethylcarbamoyl-7-(4-fluorophenyl)-8-(pyridin-4-yl)-1,2,3,4-tetrahydropyrazolo[5,1-c][1,2,4]triazine (120 mg).

mp: 235°–240° C.

NMR (CDCl$_3$:CD$_3$OD=9:1, δ): 1.12 (3H, t, J=7 Hz), 3.25 (2H, q, J=7 Hz), 4.07 (2H, t, J=6 Hz), 4.20 (2H, t, J=6 Hz), 7.04 (2H, t, J=9 Hz), 7.14 (2H, d, J=6 Hz), 7.40 (2H, dd, J=6 Hz and 9 Hz), 8.47 (2H, d, J=6 Hz)

EXAMPLE 10

The following compounds were obtained according to a similar manner to that of Example 9.

(1) 7-(4-Fluorophenyl)-2-[phenyl (thiocarbamoyl)]-8-(pyridin-4-yl)-1,2,3,4-tetrahydropyrazolo[5,1-c][1,2,4]triazine mp: 197°–200° C.

NMR (CDCl$_3$, δ): 4.40 (2H, t, J=6 Hz), 4.83 (2H, t, J=6 Hz), 7.06 (2H, t, J=9 Hz), 7.15–7.50 (10H, m), 8.48 (2H, d, J=6 Hz), 9.20 (1H, s)

(2) 7-(4-Fluorophenyl)-2-phenylcarbamoyl-8-(pyridin-4-yl)-1,2,3,4-tetrahydropyrazolo[5,1-c][1,2,4]triazine mp: 180°–182° C.

NMR (CDCl$_3$, δ): 4.17 (2H, t, J=6 Hz), 4.28 (2H, t, J=6 Hz ), 6.95–7.10 (3H, m), 7.15–7.45 (9H, m), 8.12 (1H, s), 8.51 (2H, d, J=6 Hz)

(3) 2-Carbamoyl-7-(4-fluorophenyl)-8-(pyridin-4-yl)-1,2,3,4-tetrahydropyrazolo[5,1-c][1,2,4]triazine mp: 141°–145° C.

NMR (CDCl$_3$:CD$_3$OD=9:1, δ): 4.06 (2H, t, J=6 Hz), 4.23 (2H, t, J=6 Hz), 7.07 (2H, t, J=9 Hz), 7.25 (2H, d, J=6 Hz), 7.40 (2H, dd, J=6 Hz and 9 Hz), 8.43 (2H, d, J=6 Hz)

EXAMPLE 11

A mixture of 7-(4-fluorophenyl)-8-(pyridin-4-yl)-1,2,3,4-tetrahydropyrazolo[5,1-c][1,2,4]triazine (74 mg) and N,N'-disuccinimidylcarbonate (77 mg) in dry N,N-dimethylformamide (2 ml) was stirred at ambient temperature for 1 hour. To the mixture was added diethylamine (0.13 ml) and the mixture was stirred at ambient temperature for 3 hours. The reaction mixture was poured into cold water and the separated oil was extracted with ethyl acetate. The extract was washed with brine, dried and concentrated in vacuo. The residue was crystallized from ethyl acetate to give 2-diethylcarbamoyl-7-(4-fluorophenyl)-8-(pyridin-4-yl)-1,2,3,4-tetrahydropyrazolo[5,1-c][1,2,4]triazine (80 mg).

mp: 223°–226° C.

NMR (CDCl$_3$:CD$_3$OD=9:1, δ): 1.01 (6H, t, J=7 Hz), 3.27 (4H, q, J=7 Hz), 3.84 (2H, t, J=6 Hz), 4.35 (2H, t, J=6 Hz), 7.03 (2H, t, J=9 Hz), 7.15 (2H, d, J=6 Hz), 7.40 (2H, dd, J=6 Hz and 9 Hz), 8.40 (2H, d, J=6 Hz)

EXAMPLE 12

The following compounds were obtained according to a similar manner to that of Example 11.

(1) 7-(4-Fluorophenyl)-2-morpholinocarbonyl-8-(pyridin-4-yl)-1,2,3,4-tetrahydropyrazolo[5,1-c][1,2,4]triazine mp: 232°–234° C.

NMR (CDCl$_3$:CD$_3$OD=9:1, δ): 3.52 (4H, t, J=6 Hz), 3.63 (4H, t, J=6 Hz), 3.86 (2H, t, J=6 Hz), 4.35 (2H, t, J=6 Hz), 7.06 (2H, t, J=9 Hz), 7.17 (2H, d, J=6 Hz), 7.41 (2H, dd, J=6 Hz and 9 Hz), 8.41 (2H, d, J=6 Hz)

(2) 2-Bis (2-hydroxyethyl)carbamoyl-7-(4-fluorophenyl)-8-(pyridin-4-yl)-1,2,3,4-tetrahydropyrazolo[5,1-c][1,2,4]triazine mp: 118°–121° C.

NMR (CDCl$_3$:CD$_3$OD=1:1, δ): 3.50 (4H, t, J=6 Hz), 3.62 (4H, t, J=6 Hz), 3.89 (2H, t, J=6 Hz), 7.07 (2H, t, J=9 Hz), 7.18 (2H, d, J=6 Hz), 7.38 (2H, dd, J=6 Hz and 9 Hz), 8.49 (2H, d, J=6 Hz)

(3) 2-Cyclohexylcarbamoyl-7-(4-fluorophenyl)-8-(pyridin-4-yl)-1,2,3,4-tetrahydropyrazolo[5,1-c][1,2,4]triazine mp: 181°–183° C.

NMR (CDCl$_3$, δ): 1.00–1.50 (4H, m), 1.50–1.80 (4H, m), 1.80–2.00 (2H, m), 3.60 (1H, m), 4.07 (2H, t, J=6 Hz), 4.23 (2H, t, J=6 Hz), 5.91 (1H, d, J=5 Hz), 6.10 (1H, s), 7.03 (2H, t, J=9 Hz), 7.11 (2H, d, J=6 Hz), 7.42 (2H, dd, J=6 Hz and 9 Hz), 8.53 (2H, d, J=6 Hz)

(4) 7-(4-Fluorophenyl)-2-(piperidin-1-yl)carbamoyl-8-(pyridin-4-yl)-1,2,3,4-tetrahydropyrazolo[5,1-c][1,2,4]triazine mp: 140°–141° C.

NMR (CDCl$_3$:CD$_3$OD=9:1, δ): 1.39 (2H, m), 1.65 (4H, m), 2.70 (4H, t, J=5 Hz), 4.30 (2H, t, J=6 Hz), 4.23 (2H, t, J=6 Hz), 7.07 (2H, t, J=9 Hz), 7.15 (2H, d, J=6 Hz), 7.38 (2H, dd, J=6 Hz and 9 Hz), 8.47 (2H, d, J=6 Hz)

(5) 7-(4-Fluorophenyl)-2-methoxycarbamoyl-8-(pyridin-4-yl)-1,2,3,4-tetrahydropyrazolo[5,1-c][1,2,4]triazine mp: 209°–210° C.

NMR (CDCl$_3$:CD$_3$OD=9:1, δ): 3.73 (3H, s), 4.07 (2H, t, J=6 Hz), 4.26 (2H, t, J=6 Hz), 7.07 (2H, t, J=9 Hz), 7.18 (2H, d, J=6 Hz), 7.40 (2H, dd, J=6 Hz and 9 Hz), 8.42 (2H, d, J=6 Hz)

(6) 7-(4-Fluorophenyl)-2-(2-hydroxyethylcarbamoyl)-8-(pyridin-4-yl)-1,2,3,4-tetrahydropyrazolo[5,1-c][1,2,4]triazine mp: 139°–140° C. (dec.)

NMR (DMSO-d$_6$, δ): 3.13 (2H, m), 3.38 (2H, m), 3.85 (2H, t, J=6 Hz), 4.07 (2H, t, J=6 Hz), 4.65 (1H, t, J=5 Hz), 6.85 (1H, t, J=5 Hz), 7.20 (2H, t, J=9 Hz), 7.27 (2H, d, J=5 Hz), 7.37 (2H, dd, J=6 Hz and 9 Hz), 8.47 (2H, d, J=5 Hz), 8.50 (1H, s)

EXAMPLE 13

A mixture of 3-indolylacetic acid (57 mg, 0.325 mmol), 3-(3-dimethylaminopropyl)-1-ethylcarbodiimide (50 mg, 0.325 mmol) and 1-hydroxybenzotriazole (44 mg, 0.325 mmol) in N,N-dimethylformamide (0.6 ml) was stirred for 1 hour at ambient temperature. Then to the mixture was added 7-(4-fluorophenyl)-8-(pyridin-4-yl)-1,2,3,4-tetrahydropyrazolo[5,1-c][1,2,4]triazine (80 mg, 0.271 mmol) in N,N-dimethylformamide (1 ml). After stirring for 2 hours, the mixture was diluted with water and extracted with ethyl acetate. The organic phase was washed with water and brine, dried over sodium sulfate and concentrated in vacuo. The residue was purified by crystallization from ethyl acetate to give 7-(4-fluorophenyl)-2-(3-indolylacetyl)-8-(pyridin-4-yl)-1,2,3,4-tetrahydropyrazolo[5,1-c][1,2,4]triazine (87 mg).

mp: 212°–214° C.

NMR (CDCl$_3$+CD$_3$OD, δ): 4.02–4.13 (4H, m), 4.18–4.27 (2H, m), 6.96–7.24 (7H, m), 7.32–7.42 (3H, m), 7.58 (1H, d, J=8 Hz), 8.37 (2H, d, J=6 Hz)

EXAMPLE 14

The following compounds were obtained according to a similar manner to that of Example 13.

(1) 2-tert-Butoxycarbonylaminoacetyl-7-(4-fluorophenyl)-8-(pyridin-4-yl)-1,2,3,4-tetrahydropyrazolo[5,1-c][1,2,4]triazine NMR (CDCl$_3$δ): 1.45 (9H, s), 4.10–4.20 (2H, m), 4.20–4.35 (4H, m), 5.20–5.30 (1H, m), 6.70 (1H, br s), 7.05 (2H, t, J=9 Hz), 7.15 (2H, d, J=6 Hz), 7.35 (2H, dd, J=6 Hz and 9 Hz), 8.45 (2H, d, J=6 Hz)

(2) 7-(4-Fluorophenyl)-2-(2-methoxy-2-methylpropionyl)-8-(pyridin-4-yl)-1,2,3,4-tetrahydropyrazolo[5,1-c][1,2,4]triazine mp: 114°–116° C.

NMR (CDCl$_3$, δ): 1.50 (6H, s), 3.28 (3H, s), 4.20–4.36 (3H, m), 4.64–4.83 (1H, m), 7.03 (2H, t, J=9 Hz), 7.10 (2H, d, J=6 Hz), 7.42 (2H, d, J=6.9 Hz), 8.50–8.56 (3H, m)

(3) 7-(4-Fluorophenyl)-2-[(R)-(methoxy)(phenyl)acetyl]-8-(pyridin-4-yl)-1,2,3,4-tetrahydropyrazolo[5,1-c][1,2,4]triazine mp: 213°–215° C.

NMR (CDCl$_3$, δ): 3.34 (3H, s), 3.70–3.88 (1H, m), 4.20–4.30 (2H, m), 4.45–4.58 (1H, m), 5.77 (1H, s), 5.88 (1H, s), 6.98–7.08 (4H, m), 7.27–7.33 (5H, m), 7.38 (2H, dd, J=6 Hz and 9 Hz), 8.56 (2H, d, J=6 Hz)

(4) 2-[(Biphenyl-4-yl)acetyl]-7-(4-fluorophenyl)-8-(pyridin-4-yl)-1,2,3,4-tetrahydropyrazolo[5,1-c][1,2,4]triazine mp: 153° C.

NMR (CDCl$_3$, δ): 3.98 (2H, s), 4.12–4.20 (2H, m), 4.20–4.32 (2H, m), 6.04 (1H, s), 7.03 (2H, t, J=9 Hz), 7.08 (2H, d, J=6 Hz), 7.23–7.57 (11H, m), 8.50 (2H, d, J=6 Hz)

(5) 2-[(2,6-Dichlorophenyl)acetyl]-7-(4-fluorophenyl)-8-(pyridin-4-yl)-1,2,3,4-tetrahydropyrazolo[5,1-c][1,2,4]triazine mp: >250° C.

NMR (CDCl$_3$+CD$_3$OD, δ): 4.15–4.24 (2H, m), 4.24–4.37 (4H, m), 7.06 (2H, t, J=9 Hz), 7.10–7.33 (5H, m), 7.43 (2H, dd, J=6 Hz and 9 Hz), 8.48 (2H, d, J=6 Hz)

(6) 2-(N,N-Dimethylaminoacetyl)-7-(4-flurophenyl)-8-(pyridin-4-yl)-1,2,3,4-tetrahydropyrazolo[5,1-c][1,2,4]triazine dihydrochloride mp: >250° C.

NMR (DMSO-d$_6$, δ): 2.82 (6H, s), 4.10 (2H, t, J=5 Hz), 4.25 (2H, t, J=5 Hz), 4.40 (2H, s), 7.30 (2H, t, J=9 Hz), 7.47 (2H, dd, J=6 Hz and 9 Hz), 7.79 (2H, d, J=6 Hz), 8.70 (2H, d, J=6 Hz), 10.12 (1H, s)

(7) 7-(4-Fluorophenyl)-2-(phenylthioacetyl)-8-(pyridin-4-yl)-1,2,3,4-tetrahydropyrazolo[5,1-c][1,2,4]triazine hydrochloride mp: 235°–238° C.

NMR (DMSO-d$_6$, δ): 3.95–4.20 (6H, m), 7.10–7.40 (7H, m), 7.49 (2H, dd, J=6 Hz and 9 Hz), 7.69 (2H, d, J=6 Hz), 8.68 (2H, d, J=6 Hz), 9.69 (1H, s)

(8) 7-(4-Fluorophenyl)-8-(pyridin-4-yl)-1,2,3,4-tetrahydro-2-[(3-trifluoromethylphenyl)acetyl]pyrazolo[5,1-c][1,2,4]triazine hydrochloride mp: 254° C. (dec.)

NMR (CDCl$_3$+CD$_3$OD, δ): 4.05 (2H, s) 4.17–4.39 (4H, m), 7.13 (2H, t, J=9 Hz), 7.24–7.42 (6H, m), 7.62–7.74 (2H, m), 8.32–8.50 (2H, m)

(9) 2-[(3,4-Dimethoxyphenyl)acetyl]-7-(4-fluorophenyl)-8-(pyridin-4-yl)-1,2,3,4-tetrahydropyrazolo[5,1-c][1,2,4]triazine hydrochloride NMR (CDCl$_3$, δ): 3.73 (6H, s), 3.96 (2H, s), 4.18–4.26 (4H, m), 6.62 (1H, s), 6.64 (2H, d, J=8 Hz), 7.13 (2H, t, J=9 Hz), 7.37 (2H, dd, J=6 Hz and 9 Hz), 7.70–7.77 (2H, m), 8.10–8.20 (2H, m), 9.60 (1H, br s)

(10) 2-(Acetylaminoacetyl )-7-(4-fluorophenyl)-8-(pyridin-4-yl)-1,2,3,4-tetrahydropyrazolo[5,1-c][1,2,4]triazine hydrochloride mp: 239°–243° C.

NMR (DMSO-d$_6$, δ): 1.87 (3H, s), 4.01 (2H, t, J=5 Hz), 4.12 (2H, d, J=6 Hz), 4.20 (2H, t, J=5 Hz), 7.30 (2H, t, J=9 Hz), 7.48 (2H, dd, J=6 Hz and 9 Hz), 7.69 (2H, d, J=6 Hz), 8.11 (1H, t, J=6 Hz), 8.70 (2H, d, J=6 Hz), 9.64 (1H, s)

EXAMPLE 15

To a solution of 2-acetyl-7-(4-fluorophenyl)-8-(pyridin-4-yl)-1,2,3,4-tetrahydropyrazolo[5,1-c][1,2,4]triazine (59 mg) in tetrahydrofuran was added borane-tetrahydrofuran complex (1.0M solution in tetrahydrofuran, 1 ml) dropwise. The solution was stirred at ambient temperature for 5 hours and to the solution was added dropwise 1N-hydrochloric acid (3 ml). The solution was stirred at 80° C. for 20 minutes and the tetrahydrofuran was evaporated. Then, the aqueous solution was neutralized with an aqueous saturated sodium bicarbonate solution and the separated oil was extracted with dichloromethane. The extract was dried and concentrated in vacuo. The residue was purified by column chromatography on silica gel and the obtained oil was crystallized from ethyl acetate to give 2-ethyl-7-(4-fluorophenyl)-8-(pyridin-4-yl)-1,2,3,4-tetrahydropyrazolo[5,1-c][1,2,4]triazine (30 ml).

mp: 144°–145° C.

NMR (CDCl$_3$, δ): 1.23 (3H, t, J=7 Hz), 2.88 (2H, q, J=7 Hz), 3.37 (2H, t, J=6 Hz), 4.25 (2H, t, J=6 Hz), 6.02 (1H, s), 7.04 (2H, t, J=9 Hz), 7.22 (2H, d, J=6 Hz), 7.40 (2H, dd, J=6 Hz and 9 Hz), 8.40 (2H, d, J=6 Hz)

EXAMPLE 16

The following compounds were obtained according to a similar manner to that of Example 15.

(1) 2-(3,4-Dichlorophenyl)methyl-7-(4-fluorophenyl)-8-(pyridin-4-yl)-1,2,3,4-tetrahydropyrazolo[5,1-c][1,2,4]triazine mp: 188°–191° C.

NMR (CDCl$_3$, δ): 3.40 (2H, t, J=6 Hz), 3.93 (2H, s), 4.30 (2H, t, J=6 Hz), 5.68 (1H, s), 6.99 (2H, d, J=6 Hz), 7.05 (2H, t, J=9 Hz), 7.20 (1H, d, J=8 Hz), 7.35–7.55 (4H, m), 8.41 (2H, d, J=6 Hz)

(2) 7-(4-Fluorophenyl)-2-isobutyl-8-(pyridin-4-yl)-1,2,3,4-tetrahydropyrazolo[5,1-c][1,2,4]triazine mp: 159°–162° C.

NMR (CDCl$_3$, δ): 0.98 (6H, d, J=7 Hz), 1.94 (1H, quint, J=7 Hz), 2.58 (2H, d, J=7 Hz), 3.32 (2H, t, J=6 Hz), 4.25 (2H, t, J=6 Hz), 5.58 (1H, s), 7.03 (2H, t, J=9 Hz), 7.09 (2H, d, J=6 Hz), 7.43 (2H, dd, J=6 Hz and 9 Hz), 8.47 (2H, d, J=6 Hz)

(3) 2-Cyclopropylmethyl-7-(4-fluorophenyl)-8-(pyridin-4-yl)-1,2,3,4-tetrahydropyrazolo[5,1-c][1,2,4]triazine mp: 137°–139° C.

NMR (CDCl$_3$, δ): 0.29 (2H, m), 0.56 (2H, m), 0.98 (1H, m), 2.71 (2H, d, J=7 Hz), 3.42 (2H, t, J=6 Hz), 4.23 (2H, t, J=6 Hz), 5.95 (1H, s), 7.03 (2H, t, J=9 Hz), 7.09 (2H, d, J=6 Hz), 7.42 (2H, dd, J=6 Hz and 9 Hz), 8.50 (2H, d, J=6 Hz)

(4) 2-(3,3-Dimethylbutyl)-7-(4-fluorophenyl)-8-(pyridin-4-yl)-1,2,3,4-tetrahydropyrazolo[5,1-c][1,2,4]triazine mp: 185° C. (dec.)

NMR (CDCl$_3$, δ): 0.94 (9H, s), 1.50–1.60 (2H, m), 2.75–2.85 (2H, m), 3.35 (2H, t, J=6 Hz), 4.25 (2H, t, J=6 Hz), 7.02 (2H, t, J=9 Hz), 7.10 (2H, d, J=6 Hz), 7.43 (2H, dd, J=6 Hz and 9 Hz), 8.48 (2H, d, J=6 Hz)

(5) 7-(4-Fluorophenyl)-2-neopentyl-8-(pyridin-4-yl)-1,2,3,4-tetrahydropyrazolo[5,1-c][1,2,4]triazine mp: 174° C. (dec.)

NMR (CDCl$_3$, δ): 1.00 (9H, s), 2.59 (2H, s), 3.30 (2H, t, J=5 Hz), 4.25 (2H, t, J=5 Hz), 5.70 (1H, s), 7.03 (2H, t, J=9 Hz), 7.08 (2H, d, J=6 Hz), 7.43 (2H, dd, J=6 Hz and 9 Hz), 8.46 (2H, d, J=6 Hz)

(6) 2-Cyclohexylmethyl-7-(4-fluorophenyl)-8-(pyridin-4-yl)-1,2,3,4-tetrahydropyrazolo[5,1-c][1,2,4]triazine mp: 120°–135° C. (dec.)

NMR (CDCl$_3$, δ): 0.84–1.05 (2H, m), 1.13–1.40 (4H, m), 1.54–1.90 (5H, m), 2.60 (2H, d, J=8 Hz), 3.29 (2H, t, J=6 Hz), 4.24 (2H, t, J=6 Hz), 5.56 (1H, s), 7.02 (2H, t, J=9 Hz), 7.08 (2H, d, J=6 Hz), 7.43 (2H, dd, J=6 Hz and 9 Hz), 8.47 (2H, d, J=6 Hz)

(7) 2-(2,2-Dimethylbutyl)-7-(4-fluorophenyl)-8-(pyridin-4-yl)-1,2,3,4-tetrahydropyrazolo[5,1-c][1,2,4]triazine mp: 148°–151° C. (dec.)

NMR (CDCl$_3$, δ): 0.83 (3H, t, J=8 Hz), 0.94 (6H, s), 1.36 (2H, q, J=8 Hz), 2.59 (2H, s), 3.28 (2H, t, J=6 Hz), 4.25 (2H, t, J=6 Hz), 5.67 (1H, s), 7.02 (2H, t, J=9 Hz), 7.07 (2H, d, J=6 Hz), 7.43 (2H, dd, J=6 Hz and 9 Hz), 8.46 (2H, d, J=6 Hz)

EXAMPLE 17

To a mixture of 7-(4-fluorophenyl)-8-(pyridin-4-yl)-1,2,3,4-tetrahydropyrazolo[5,1-c][1,2,4]triazine (89 mg) and sodium cyanoborohydride (63 mg) in methanol (1 ml) was added acetone (0.1 ml) with ice cooling. The pH of the mixture was adjusted to 3 to 4 with 1N hydrochloric acid and the solution was stirred at 4° C. for 30 minutes. Then, the solution was neutralized with an aqueous saturated sodium bicarbonate solution and poured into cold water. The separated oil was extracted with ethyl acetate and the extract was washed with brine, dried and concentrated in vacuo. The residue was crystallized from diethyl ether to give 7-(4-fluorophenyl)-2-isopropyl-8-(pyridin-4-yl)-1,2,3,4-tetrahydropyrazolo[5,1-c][1,2,4]triazine (75 mg).

NMR (CDCl$_3$, δ): 1.20 (6H, d, J=7 Hz), 3.09 (1H, m), 3.42 (2H, t, J=6 Hz), 4.21 (2H, t, J=6 Hz), 5.62 (1H, s), 7.03 (2H, t, J=9 Hz), 7.10 (2H, d, J=6 Hz), 7.42 (2H, dd, J=6 Hz and 9 Hz), 8.48 (2H, d, J=6 Hz)

EXAMPLE 18

The following compounds were obtained according to a similar manner to that of Example 17.

(1) 2-(Adamantan-2-yl)-7-(4-fluorophenyl)-8-(pyridin-4-yl)-1,2,3,4-tetrahydropyrazolo[5,1-c][1,2,4]triazine mp: 224° C. (dec.)

NMR (CDCl$_3$, δ): 1.47–2.18 (14H, m), 2.90 (1H, m), 3.44 (2H, t, J=6 Hz), 4.18 (2H, t, J=6 Hz), 5.63 (1H, s), 7.03 (2H, t, J=9 Hz), 7.08 (2H, d, J=6 Hz), 7.44 (2H, dd, J=6 Hz and 9 Hz), 8.48 (2H, d, J=6 Hz)

(2) 2-Cyclohexyl-7-(4-Fluorophenyl)-8-(pyridin-4-yl)-1,2,3,4-tetrahydropyrazolo[5,1-c][1,2,4]triazine NMR (CDCl$_3$, δ): 1.10–1.40 (4H, m), 1.55–2.10 (6H, m), 2.73 (1H, m), 3.45 (2H, t, J=6 Hz), 4.19 (2H, t, J=6 Hz), 5.67 (1H, s), 7.03 (2H, t, J=9 Hz), 7.10 (2H, d, J=6 Hz), 7.42 (2H, dd, J=6 Hz and 9 Hz), 8.48 (2H, d, J=6 Hz)

(3) 7-(4-Fluorophenyl)-8-(pyridin-4-yl)-2-(tetrahydropyran-4-yl)-1,2,3,4-tetrahydropyrazolo[5,1-c][1,2,4]triazine NMR (CDCl$_3$, δ): 1.50–1.80 (2H, m), 1.85–2.05 (2H, m), 2.98 (1H, m), 3.30–3.50 (4H, m), 3.95–4.10 (2H, m), 4.21 (2H, t, J=6 Hz), 5.70 (1H, s), 7.03 (2H, t, J=9 Hz), 7.09 (2H, d, J=6 Hz), 7.41 (2H, dd, J=6 Hz and 9 Hz), 8.48 (2H, d, J=6 Hz)

(4) 2-(1-Acetylpiperidin-4-yl)-7-(4-fluorophenyl)-8-(pyridin-4-yl)-1,2,3,4-tetrahydropyrazolo[5,1-c][1,2,4]triazine NMR (CDCl$_3$, δ): 1.52 (2H, m), 1.99 (2H, m), 2.11 (3H, s), 2.78 (1H, m), 2.98 (1H, m), 3.15 (1H, m), 3.47 (2H, t, J=6 Hz), 3.85 (1H, m), 4.22 (2H, t, J=6 Hz), 4.51 (1H, m), 5.69 (1H, s), 7.03 (2H, t, J=9 Hz), 7.09 (2H, d, J=6 Hz), 7.41 (2H, dd, J=6 Hz and 9 Hz), 8.47 (2H, d, J=6 Hz)

(5) 7-(4-Fluorophenyl)-2-(1-methylpiperidin-4-yl)-8-(pyridin-4-yl)-1,2,3,4-tetrahydropyrazolo[5,1-c][1,2,4]triazine NMR (CDCl$_3$:CD$_3$OD=9:1, δ): 1.50–1.75 (2H, m), 1.90–2.15 (4H, m), 2.30 (3H, s), 2.65–3.00 (3H, m), 3.46 (2H, t, J=6 Hz), 4.19 (2H, t, J=6 Hz), 7.07 (2H, t, J=9 Hz), 7.12 (2H, d, J=6 Hz), 7.39 (2H, dd, J=6 Hz and 9 Hz), 8.38 (2H, d, J=6 Hz)

(6) 7-(4-Fluorophenyl)-2-(1-methoxycarbonylethyl)-8-(pyridin-4-yl)-1,2,3,4-tetrahydropyrazolo[5,1-c][1,2,4]triazine mp: 132°–134° C.

NM (CDCl$_3$, δ): 1.50 (3H, d, J=7 Hz), 3.27–3.58 (2H, m), 3.78 (3H, s), 3.82 (1H, q, J=7 Hz), 4.10–4.40 (2H, m), 6.04 (1H, s), 7.03 (2H, t, J=9 Hz), 7.10 (2H, d, J=6 Hz), 7.41 (2H, dd, J=6 Hz and 9 Hz), 8.48 (2H, d, J=6 Hz)

(7) 7-(4-Fluorophenyl)-2-(indan-2-yl)-8-(pyridin-4-yl)-1,2,3,4-tetrahydropyrazolo[5,1-c][1,2,4]triazine mp: 232° C. (dec.)

NMR (CDCl$_3$, δ): 2.99–3.26 (4H, m), 3.48 (2H, t, J=6 Hz), 3.90 (1H, t, J=8 Hz), 4.30 (2H, t, J=6 Hz), 5.68 (1H, s), 7.03 (2H, t, J=9 Hz), 7.08 (2H, d, J=6 Hz), 7.15–7.25 (4H, m), 7.41 (2H, dd, J=6 Hz and 9 Hz), 8.48 (2H, d, J=6 Hz)

(8) 2-[(E)-Cinnamyl]-7-(4-fluorophenyl)-8-(pyridin-4-yl)-1,2,3,4-tetrahydropyrazolo[5,1-c][1,2,4]triazine mp: 178°–183° C.

NMR (CDCl₃, δ): 3.43 (2H, t, J=6 Hz), 3.63 (2H, d, J=6 Hz), 4.27 (2H, t, J=6 Hz), 5.80 (1H, br s), 6.27 (1H, td, J=6 Hz and 15 Hz), 6.60 (1H, d, J=15 Hz), 6.98–7.09 (4H, m), 7.27–7.36 (5H, m), 7.43 (2H, dd, J=6 Hz and 9 Hz), 8.40 (2H, d, J=6 Hz)

(9) 2-(3,3-Dimethyl-1,5-dioxaspiro[5,5]undecan-9-yl)-7-(4-fluorophenyl)-8-(pyridin-4-yl)-1,2,3,4-tetrahydropyrazolo[5,1-c][1,2,4]triazine mp: 186° C. (dec.)

NMR (CDCl₃, δ): 0.98 (6H, s), 1.44–1.76 (4H, m), 1.85–1.98 (2H, m), 2.15–2.28 (2H, m), 2.78–2.91 (1H, m), 3.46 (2H, t, J=6 Hz), 3.52 (4H, d, J=4 Hz), 4.20 (2H, t, J=6 Hz), 5.60 (1H, s), 7.03 (2H, t, J=9 Hz), 7.09 (2H, d, J=6 Hz), 7.41 (2H, dd, J=6 Hz and 9 Hz), 8.46 (2H, d, J=6 Hz)

EXAMPLE 19

A mixture of 2-acetoxyacetyl-7-(4-fluorophenyl)-8-(pyridin-4-yl)-1,2,3,4-tetrahydropyrazolo[5,1-c][1,2,4]triazine (75 mg, 0.190 mmol) and an aqueous sodium hydroxide solution (1N, 0.38 ml, 0.380 mmol) in ethanol (1.5 ml) was stirred for 30 minutes at ambient temperature. After dilution of an aqueous saturated ammonium chloride solution, the mixture was extracted with ethyl acetate. The extracts were dried over sodium sulfate, and concentrated in vacuo. The residue was purified by chromatography on silica gel (eluent:dichloromethane/methanol; 50/1~10/1), and the obtained amorphous product was crystallized from diisopropyl ether to give 7-(4-fluorophenyl)- 2-hydroxyacetyl-8-(pyridin-4-yl)-1,2,3,4-tetrahydropyrazolo[5,1-c][1,2,4]triazine (20 mg).

mp: 133° C. (dec.)

NMR (DMSO-d₆, δ): 3.95–4.05 (2H, m), 4.10–4.20 (2H, m), 4.25 (2H, d, J=6 Hz), 4.75 (1H, t, J=6 Hz), 7.15 (2H, d, J=6 Hz), 7.25 (2H, t, J=9 Hz), 7.40 (2H, dd, J=6 Hz and 9 Hz), 8.50 (2H, d, J=6 Hz), 8.55 (1H, s)

EXAMPLE 20

A mixture of 2-(4-acetoxybenzoyl)-7-(4-fluorophenyl)-8-(pyridin-4-yl)-1,2,3,4-tetrahydropyrazolo[5,1-c][1,2,4]triazine (65 mg, 0.142 mmol) and potassium carbonate (20 mg, 0.142 mmol) in methanol (1.3 ml) was stirred for 30 minutes at ambient temperature. The mixture was adjusted to pH 6 with an aqueous saturated ammonium chloride solution, and extracted with ethyl acetate. The organic phase was washed with water and brine, dried over sodium sulfate, and concentrated in vacuo. The residue was purified by chromatography on silica gel (eluent:dichloromethane/methanol; 30/1~20/1), and the obtained amorphous product was crystallized from diisopropyl ether to give 7-(4-fluorophenyl)-2-(4-hydroxybenzoyl)-8-(pyridin-4-yl)-1,2,3,4-tetrahydropyrazolo[5,1-c][1,2,4]triazine (37 mg).

mp: 222° C. (dec.)

NMR (CDCl₃+CD₃OD, δ): 4.20–4.40 (4H, m), 6.85 (2H, d, J=9 Hz), 6.95–7.10 (4H, m), 7.35 (2H, dd, J=6 Hz and 9 Hz), 7.55 (2H, d, J=9 Hz), 8.30 (2H, d, J=6 Hz)

EXAMPLE 21

2-tert-Butoxycarbonylaminoacetyl-7-(4-fluorophenyl)-8-(pyridin-4-yl)-1,2,3,4-tetrahydropyrazolo[5,1-c][1,2,4]triazine (50 mg) was dissolved in trifluoroacetic acid (0.5 ml). The solution was stirred at ambient temperature for 30 minutes and concentrated in vacuo. The residue was dissolved in water and the solution was neutralized with an aqueous saturated sodium bicarbonate solution. The separated oil was extracted with a mixture of dichloromethane and ethanol (7:3) and the extract was washed with water, dried and concentrated in vacuo. The residue was crystallized from ethyl acetate to give 2-aminoacetyl-7-(4-fluorophenyl)-8-(pyridin-4-yl)-1,2,3,4-tetrahydropyrazolo[5,1-c][1,2,4]triazine (30 mg).

mp: 208°–211° C.

NMR (DMSO-d₆, δ): 3.50 (2H, s), 4.01 (2H, t, J=6 Hz), 4.16 (2H, t, J=6 Hz), 7.19 (2H, d, J=6 Hz), 7.22 (2H, t, J=9 Hz), 7.40 (2H, dd, J=6 Hz and 9 Hz), 8.49 (2H, d, J=6 Hz)

EXAMPLE 22

A mixture of 2-chloroacetyl-7-(4-fluorophenyl)-8-(pyridin-4-yl)-1,2,3,4-tetrahydropyrazolo[5,1-c][1,2,4]triazine (80 mg, 0.215 mmol), morpholine (37 mg, 0.430 mmol), and triethylamine (22 mg, 0.215 mmol) in 1,2-dichloroethane (2 ml) was stirred for 24 hours at ambient temperature. After dilution of dichloromethane, the mixture was washed with an aqueous saturated sodium bicarbonate solution, and brine. The organic phase was dried over sodium sulfate, and concentrated in vacuo. The residue was purified by chromatography on silica gel (eluent:ethyl acetate ethyl acetate/methanol; 20/1), and the obtained oil was crystallized from diisopropyl ether to give 7-(4-fluorophenyl)-2-morpholinoacetyl-8-(pyridin-4-yl)-1,2,3,4-tetrahydropyrazolo[5,1-c][1,2,4]triazine (50 mg).

NMR (CDCl₃, δ): 2.50 (4H, t, J=4.5 Hz), 3.35 (2H, s), 3.65 (4H, t, J=4.5 Hz), 4.20 (2H, d, J=6 Hz), 4.30 (2H, d, J=6 Hz), 7.05 (2H, t, J=9 Hz), 7.10 (2H, d, J=6 Hz), 7.40 (2H, dd, J=6 Hz and 9 Hz), 7.95 (1H, br s), 8.50 (2H, d, J=6 Hz)

EXAMPLE 23

To a mixture of 7-(4-fluorophenyl)-8-(pyridin-4-yl)-1,2,3,4-tetrahydropyrazolo[5,1-c][1,2,4]triazine (118 mg) and pyridine (64 mg) in N-methyl-1-pyrrolidone (2 ml) was added phenylacetyl chloride (65 mg) under nitrogen atmosphere with ice cooling. After stirring for 1 hour at 4° C., the reaction mixture was poured into cold water. The separated oil was extracted with ethyl acetate and the extract was washed with brine, dried and concentrated in vacuo. The residue was purified by column chromatography on silica gel and the obtain oil was dissolved in 10% methanolic hydrogen chloride (1 ml). The resulting clear solution was concentrated in vacuo. The residue was crystallized from ethyl acetate to give 7-(4-fluorophenyl)-2-phenylacetyl-8-(pyridin-4-yl)-1,2,3,4-tetrahydropyrazolo[5,1-c][1,2,4]triazine hydrochloride (130 mg).

mp: 208°–212° C.

NMR (DMSO-d₆, δ) 3.87 (2H, s), 4.07 (2H, t, J=5 Hz), 4.18 (2H, t, J=5 Hz), 7.00–7.20 (5H, m), 7.29 (2H, t, J=9 Hz), 7.43 (2H, dd, J=6 Hz and 9 Hz), 7.66 (2H, d, J=6 Hz), 8.71 (2H, d, J=6 Hz), 9.63 (1H, s)

EXAMPLE 24

The following compounds were obtained according to a similar manner to that of Example 23.

(1) 7-(4-Fluorophenyl)-2-pentanoyl-8-(pyridin-4-yl)-1,2,3,4-tetrahydropyrazolo[5,1-c][1,2,4]triazine hydrochloride mp: 175° C. (dec.)

NMR (CD₃Cl, δ): 0.90 (3H, t, J=6 Hz), 1.25–1.45 (2H, m), 1.55–1.70 (2H, m), 2.55 (2H, t, J=6 Hz), 4.10–4.30 (4H, m), 7.15 (2H, t, J=9 Hz), 7.40 (2H, dd, J=6 Hz and 9 Hz), 7.80–7.90 (2H, m), 8.10–8.25 (2H, m), 9.60 (1H, br s)

(2) 7-(4-Fluorophenyl)-2-isobutyryl-8-(pyridin-4-yl)-1,2,3,4-tetrahydropyrazolo[5,1-c][1,2,4]triazine hydrochloride NMR (CDCl$_3$, δ): 1.15 (6H, d, J=7 Hz), 3.20–3.40 (1H, m), 4.15–4.30 (4H, m), 7.15 (2H, t, J=9 Hz), 7.40 (2H, dd, J=6 Hz and 9 Hz), 7.80–7.90 (2H, m), 8.15–8.30 (2H, m), 9.50 (1H, br s)

(3) 2-(3,4-Dichlorobenzoyl)-7-(4-fluorophenyl)-8-(pyridin-4-yl)-1,2,3,4-tetrahydropyrazolo[5,1-c][1,2,4]triazine hydrochloride NMR (DMSO-d$_6$, δ): 4.22 (2H, t, J=6 Hz), 4.33 (2H, t, J=6 Hz), 7.29 (2H, t, J=9 Hz), 7.40–7.60 (4H, m), 7.70 (2H, m), 7.94 (1H, s), 8.63 (2H, d, J=6 Hz), 9.99 (1H, s)

(4) 7-(4-Fluorophenyl)-2-phenylglyoxyloyl-8-(pyridin-4-yl)-1,2,3,4-tetrahydropyrazolo[5,1-c][1,2,4]triazine hydrochloride mp: 182°–191° C. (dec.)

NMR (DMSO-d$_6$, δ): 4.24 (2H, t, J=6 Hz), 4.49 (2H, t, J=6 Hz), 7.16 (2H, d, J=7 Hz), 7.26 (2H, t, J=9 Hz), 7.30–7.45 (4H, m), 7.50–7.65 (3H, m), 8.57 (2H, d, J=7 Hz), 9.77 (1H, s)

(5) 7-(4-Fluorophenyl)-8-(pyridin-4-yl)-1,2,3,4-tetrahydro-2-(4-trifluoromethylphenyl)glyoxyloylpyrazolo[5,1-c][1,2,4]triazine hydrochloride mp: 260°–265° C. (dec.)

NMR (CDCl$_3$+CD$_3$OD, δ): 4.32–4.50 (4H, m), 7.13 (2H, t, J=9 Hz), 7.30–7.43 (4H, m), 7.79 (2H, d, J=9 Hz), 7.93 (2H, d, J=9 Hz), 8.22 (2H, d, J=6 Hz)

EXAMPLE 25

To a mixture of 7-(4-fluorophenyl)-2-isobutyl-8-(pyridin-4-yl)-1,2,3,4-tetrahydropyrazolo[5,1-c][1,2,4]triazine (70 mg, 0.199 mmol) and pyridine (31 mg, 0.398 mmol) in N-methyl-2-pyrrolidone (1.2 ml) was added acetyl chloride (19 mg, 0.239 mmol) in N-methyl-2-pyrrolidone (0.3 ml) at ambient temperature. The reaction mixture was stirred for 1 hour, then aqueous saturated sodium bicarbonate and ethyl acetate were added thereto. The organic phase was separated, and washed with water, brine, and dried over sodium sulfate. The solvent was evaporated, and the obtained residue was purified by column chromatography on silica gel (eluent:dichloromethane/methanol; 100/1–40/1). The fractions containing the object compound were concentrated in vacuo and the obtained oil was crystallized from diisopropyl ether to give 1-acetyl-7-(4-fluorophenyl)-2-isobutyl-8-(pyridin-4-yl)-1,2,3,4-tetrahydropyrazolo-[5,1-c][1,2,4]triazine (57.0 mg).

mp: 194°–197° C. (dec.)

NMR (CDCl$_3$, δ): 1.05 (3H, d, J=6 Hz), 1.12 (3H, d, J=6 Hz), 1.90 (1H, m), 2.25 (3H, s), 2.57–2.69 (1H, m), 2.75–2.86 (1H, m), 3.43–3.70 (2H, m), 4.13–4.24 (1H, m), 4.33–4.50 (1H, m), 6.95–7.05 (4H, m), 7.34 (2H, dd, J=6 Hz and 9 Hz), 8.50 (2H, d, J=6 Hz)

EXAMPLE 26

The following compounds were obtained according to a similar manner to that of Example 1.

(1) 8-(2-Chloropyridin-4-yl)-7-(4-fluorophenyl)-1,2,3,4-tetrahydropyrazolo[5,1-c][1,2,4]triazine mp: 219°–221° C.

NMR (CDCl$_3$, δ): 3.48 (2H, q, J=5 Hz), 3.68 (1H, q, J=5 Hz), 4.20 (2H, t, J=5 Hz), 5.65 (1H, d, J=5 Hz), 6.94 (1H, d, J=6 Hz), 7.06 (2H, t, J=9 Hz), 7.16 (1H, s), 7.40 (2H, dd, J=6 Hz and 9 Hz), 8.20 (1H, d, J=6 Hz)

(2) 8-(2-Bromopyridin-4-yl)-7-(4-fluorophenyl)-1,2,3,4-tetrahydropyrazolo[5,1-c][1,2,4]triazine mp: 212°–216° C.

NMR (CDCl$_3$, δ): 3.32–3.44 (2H, m), 3.68 (1H, m), 4.20 (2H, t, J=5 Hz), 5.67 (1H, br s), 6.95 (1H, d, J=6 Hz), 7.07 (2H, t, J=9 Hz), 7.17 (1H, s), 7.40 (2H, dd, J=6 Hz and 9 Hz), 8.21 (1H, d, J=6 Hz)

(3) 7-(4-Fluorophenyl)-8-(2-methoxypyridin-4-yl)-1,2,3,4-tetrahydropyrazolo[5,1-c][1,2,4]triazine mp: 205°–209° C.

NMR (CDCl$_3$:CD$_3$OD=9:1, δ): 3.35 (2H, t, J=6 Hz), 3.89 (3H, s), 4.17 (2H, t, J=6 Hz), 6.60 (1H, s), 6.68 (1H, d, J=6 Hz), 7.05 (2H, t, J=9 Hz), 7.42 (2H, dd, J=6 Hz and 9 Hz), 7.98 (1H, d, J=6 Hz)

(4) 7-(4-Fluorophenyl)-8-(2-fluoropyridin-4-yl)-1,2,3,4-tetrahydropyrazolo[5,1-c][1,2,4]triazine mp: 230°–232° C.

NMR (CDCl$_3$:CD$_3$OD=9:1, δ): 3.37 (2H, t, J=6 Hz), 4.18 (2H, t, J=6 Hz), 6.77 (1H, s), 6.95 (1H, d, J=6 Hz), 7.08 (2H, t, J=9 Hz), 7.40 (2H, dd, J=6 Hz and 9 Hz), 8.02 (1H, d, J=6 Hz)

EXAMPLE 27

The following compounds were obtained according to similar manners to those of Example 3, 7 and 13.

(1) 2-Acetyl-8-(2-chloropyridin-4-yl)-7-(4-fluorophenyl)-1,2,3,4-tetrahydropyrazolo[5,1-c][1,2,4]triazine mp: 208°–209° C.

NMR (CDCl$_3$, δ): 2.34 (3H, s), 4.13–4.20 (2H, m), 4.20–4.31 (2H, m), 6.30 (1H, br s), 7.00–7.11 (3H, m), 7.24 (1H, s), 7.40 (2H, dd, J=6 Hz and 9 Hz), 8.23 (1H, d, J=6 Hz)

(2) 8-(2-Chloropyridin-4-yl)-7-(4-fluorophenyl)-2-phenylglyoxyloyl-1,2,3,4-tetrahydropyrazolo[5,1-c][1,2,4]triazine NMR (CDCl$_3$, δ): 4.30 (2H, t, J=5 Hz), 4.45 (2H, t, J=5 Hz), 6.54–6.60 (2H, m), 6.67 (1H, s), 7.03 (2H, t, J=9 Hz), 7.30 (2H, m), 7.53 (2H, t, J=9 Hz), 7.68 (1H, t, J=9Hz), 7.89–7.95 (3H, m)

(3) 2-Acetyl-8-(2-bromopyridin-4-yl)-7-(4-fluorophenyl)-1,2,3,4-tetrahydropyrazolo[5,1-c][1,2,4]triazine mp: 210°–211° C.

NMR (CDCl$_3$, δ): 2.35 (3H, s), 4.12–4.32 (4H, m), 6.30 (1H, br s), 7.00–7.12 (3H, m), 7.23 (1H, s), 7.40 (2H, dd, J=6 Hz and 9 Hz), 8.24 (1H, d, J=6 Hz)

(4) 8-(2-Bromopyridin-4-yl)-7-(4-fluorophenyl)-2-phenylglyoxyloyl-1,2,3,4-tetrahydropyrazolo[5,1-c][1,2,4]triazine NMR (CDCl$_3$, δ): 4.30 (2H, t, J=5 Hz), 4.45 (2H, t, J=5 Hz), 6.53–6.61 (2H, m), 6.68 (1H, s), 7.02 (2H, t, J=9 Hz), 7.25–7.35 (2H, m), 7.53 (2H, t, J=9 Hz), 7.66 (1H, t, J=9 Hz), 7.88–7.97 (3H, m)

(5) 7-(4-Fluorophenyl)-2-[(2-methoxyphenyl)glyoxyloyl]-8-(pyridin-4-yl)-1,2,3,4-tetrahydropyrazolo[5,1-c][1,2,4]triazine mp: 231°–245° C. (dec.)

NMR (CDCl$_3$, δ): 3.48 (3H, s), 4.24 (2H, t, J=6 Hz), 4.43 (2H, t, J=6 Hz), 6.48 (2H, d, J=6 Hz), 6.77 (1H, s), 6.84 (1H, d, J=9 Hz), 7.01 (2H, t, J=9 Hz), 7.15 (1H, dt, J=2 Hz and 9 Hz), 7.32 (2H, dd, J=6 Hz and 9 Hz), 7.57 (1H, dt, J=2 Hz and 9 Hz), 8.06–8.13 (3H, m)

(6) 2-Acetyl-7-(4-fluorophenyl)-8-(2-methoxypyridin-4-yl)-1,2,3,4-tetrahydropyrazolo[5,1-c][1,2,4]triazine mp: 148°–150° C.

NMR (CDCl$_3$:CD$_3$OD=9:1, δ): 2.28 (3H, s), 3.91 (3H, s), 4.12 (2H, t, J=6 Hz), 4.25 (2H, t, J=6 Hz), 6.67 (1H, s), 6.72 (1H, d, J=6 Hz), 7.06 (2H, t, J=9 Hz), 7.41 (2H, dd, J=6 Hz and 9 Hz), 8.02 (1H, d, J=6 Hz)

(7) 7-(4-Fluorophenyl)-8-(2-methoxypyridin-4-yl)-2-phenylglyoxyloyl-1,2,3,4-tetrahydropyrazolo[5,1-c][1,2,4]triazine mp: 129°–133° C.

NMR (CDCl₃:CD₃OD=9:1, δ): 3.81 (3H, s), 4.25 (2H, t, J=6 Hz), 4.42 (2H, t, J=6 Hz), 6.20 (1H, s), 6.28 (1H, d, J=6 Hz), 7.02 (2H, t, J=9 Hz), 7.32 (2H, dd, J=6 Hz and 9 Hz), 7.46 (2H, t, J=8 Hz), 7.61 (1H, t, J=8 Hz), 7.75–7.85 (3H, m)

(8) 2-Acetyl-7-(4-fluorophenyl)-8-(2-fluoropyridin-4-yl)-1,2,3,4-tetrahydropyrazolo[5,1-c][1,2,4]triazine mp: 204°–206° C.

NMR (CDCl₃:CD₃OD=9:1, δ): 2.28 (3H, s), 4.14 (2H, t, J=6 Hz), 4.26 (2H, t, J=6 Hz), 7.02 (1H, d, J=6 Hz), 7.10 (2H, t, J=9 Hz), 7.04 (2H, dd, J=6 Hz and 9 Hz), 8.05 (1H, d, J=6 Hz)

(9) 7-(4-Fluorophenyl)-8-(2-fluoropyridin-4-yl)-2-phenylglyoxyloyl-1,2,3,4-tetrahydropyrazolo[5,1-c][1,2,4]triazine mp: 238°–240° C.

NMR (CDCl₃:CD₃OD=9:1, δ): 4.28 (2H, t, J=6 Hz), 4.43 (2H, t, J=6 Hz), 6.35 (1H, s), 6.60 (1H, d, J=6 Hz), 7.05 (2H, t, J=9 Hz), 7.48 (2H, t, J=8 Hz), 7.62 (1H, t, J=8 Hz), 7.75–7.90 (3H, m)

(10) 2-Acetyl-7-(4-fluorophenyl)-8-(pyridin-4-yl)-1,2,3,4-tetrahydropyrazolo[5,1-c][1,2,4]triazine hydrochloride mp: 262°–270° C. (dec)

NMR (CHCl₃, δ): 2.29 (3H, s), 4.11–4.27 (4H, m), 7.12 (2H, t, J=9 Hz), 7.40 (2H, dd, J=6, 9 Hz), 7.80 (2H, d, J=6 Hz), 8.49 (2H, d, J=6 Hz), 9.57 (1H, br s)

(11) 7-(4-Fluorophenyl)-2-phenylglyoxyloyl-8-(pyridin-4yl)-1,2,3,4-tetrahydropyrazolo[5,1-c][1,2,4]triazine mp: 240.5°–242.0° C.

NMR (CDCl₃:CD₃OD=9:1, δ): 4.27 (2H, t, J=6 Hz), 4.45 (2H, t, J=6 Hz), 6.70 (2H, d, J=6 Hz), 7.01 (2H, t, J=9 Hz), 7.30 (2H, dd, J=6 Hz, 9 Hz), 7.47 (2H, t, J=8 Hz), 7.63 (1H, t, J=8 Hz), 7.81 (2H, d, J=8 Hz), 8.18 (2H, d, J=6 Hz)

EXAMPLE 28

To a suspension of 7-(4-fluorophenyl)-2-phenylglyoxyloyl-8-(pyridin-4-yl)-1,2,3,4-tetrahydropyrazolo[5,1-c][1,2,4]triazine (2.778 g) in a mixture of ethanol (14 ml) and ethyl acetate (10 ml) was added conc. sulfuric acid (0.67 g). To the resulting clear solution was added ethyl acetate (30 ml) and the solution was stirred at ambient temperature for 4 hours. The separated solid was collected and recrystallized from aqueous acetonitrile to give 7-(4-fluorophenyl)-2-phenylglyoxyloyl-8-(pyridin-4-yl)-1,2,3,4-tetrahydropyrazolo[5,1-c][1,2,4]triazine sulfate (2.7 g).

mp: 155°–157° C.

NMR (DMSO-d₆, δ): 4.25 (2H, m), 4.49 (2H, m), 7.12 (2H, d, J=7 Hz), 7.15–7.50 (6H, m), 7.50–7.70 (3H, m), 8.56 (2H, d, J=7 Hz), 9.43 (1H, s)

We claim:

1. A compound of the formula:

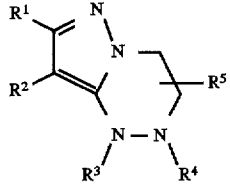

wherein $R^1$ is optionally substituted aryl or optionally substituted saturated or unsaturated, monocyclic or polycyclic heterocyclic group containing at least one hetero-atom selected from the group consisting of oxygen, sulfur, and nitrogen atoms, $R^2$ is optionally substituted aryl or optionally substituted saturated or unsaturated, monocyclic or polycyclic heterocyclic group containing at least one hetero-atom selected from the group consisting of oxygen, sulfur, and nitrogen atoms, $R^3$ is hydrogen or acyl, $R^4$ is hydrogen, lower alkyl, cyclo(lower)alkyl, cyclo(lower)alkyl-(lower)alkyl, carboxy(lower)alkyl, protected carboxy(lower)alkyl, optionally substituted ar(lower)alkyl, ar(lower)alkenyl, bridged tricyclicalkyl, optionally substituted saturated or unsaturated, monocyclic or polycyclic heterocyclic group containing at least one hetero-atom selected from the group consisting of oxygen, sulfur, and nitrogen atoms, optionally substituted dioxaspiroundecanyl, acyl, or a group of the formula:

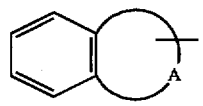

(in which A is lower alkylene), and $R^5$ is hydrogen or lower alkyl, and a pharmaceutically acceptable salt thereof.

2. A compound of claim 1, wherein $R^1$ is phenyl which may have 1 to 3 suitable substituent (s), or pyridyl which may have 1 to 3 suitable substituent(s), $R^2$ is phenyl which may have 1 to 3 suitable substituent(s) or pyridyl which may have 1 to 3 suitable substituent (s), $R^3$ is hydrogen or lower alkanoyl, $R^4$ is hydrogen; lower alkyl; cyclo(lower)alkyl; cyclo(lower)alkyl-(lower)alkyl; carboxy(lower)alkyl; esterified carboxy(lower)alkyl; phenyl(lower)alkyl which may have 1 to 3 suitable substituent(s); adamantanyl; phenyl(lower)alkenyl; tetrahydropyranyl, piperidyl or dioxaspiro decanyl, each of which may have 1 to 3 substituent(s) selected from the group consisting of lower alkyl and acyl; indanyl; lower alkanoyl which may have 1 to 3 suitable substituent(s); lower alkoxycarbonyl; lower alkoxyglyoxyloyl; lower alkylsulfonyl; cyclo(lower)alkylcarbonyl; aroyl which may have 1 to 3 suitable substituent(s); ar(lower)alkanoyl which may have 1 to 3 suitable substituent(s); ar(lower) alkenoyl; arylthio(lower)alkanoyl; arylcarbamoyl; aryl-thiocarbamoyl; arylglyoxyloyl which may have 1 to 3 suitable substituent(s); carbamoyl which may have one or two suitable substituent(s) selected from the group consisting of lower alkyl, hydroxy(lower)alkyl, protected hydroxy(lower)alkyl, lower alkoxy and cyclo (lower)alkyl; heterocycliccarbonyl; heterocyclic (lower)alkanoyl; or heterocycliccarbamoyl.

3. A compound of claim 2, wherein $R^1$ is phenyl which may have 1 to 3 substituent(s) selected from the group consisting of lower alkyl, lower alkoxy, lower alkenyl, lower alkynyl, mono (or di or tri)halo (lower)alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio and imino; or pyridyl which may have 1 to 3 substituent(s) selected from the group consisting of lower alkyl, lower alkoxy, lower alkenyl, lower alkynyl, mono (or di or tri)halo (lower)alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio and imino, $R^2$ is phenyl which may have 1 to 3 substituent(s) selected from the group consisting of lower alkyl, lower alkoxy, lower alkenyl, lower alkynyl, mono(or di or tri)halo (lower)alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio and imino; or pyridyl which may have 1 to 3 substituent(s) selected from the group consisting of lower alkyl, lower alkoxy, lower alkenyl, lower alkynyl, mono(or di or tri)halo (lower)alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio and imino, $R^4$ is hydrogen; lower alkyl; cyclo(lower)alkyl; cyclo (lower)alkyl-(lower)alkyl; carboxy(lower)alkyl; lower alkoxycarbonyl(lower)alkyl; phenyl(lower)alkyl which may have 1 to 3 substituent(s) selected from the group consisting of halogen, lower alkyl, lower alkoxy, lower alkenyl, lower alkynyl, mono(or di or tri)halo(lower) alkyl and di(lower)alkylamino; adamantanyl; phenyl (lower)alkenyl; tetrahydropyranyl, piperidyl or dioxaspiroundecanyl, each of which may have one or two substituent(s) selected from the group consisting of lower alkyl and lower alkanoyl; indanyl; lower alkanoyl which may have 1 to 3 substituent(s) selected from the group consisting of carboxy, protected carboxy, lower alkoxy, halogen, protected amino, amino, hydroxy, protected hydroxy and di(lower) alkylamino; lower alkoxycarbonyl; lower alkoxyglyoxyloyl lower alkylsulfonyl; cyclo(lower) alkylcarbonyl; benzoyl which may have 1 to 3 substituent(s) selected from the group consisting of mono(or di or tri)halo(lower)alkyl, halogen, protected hydroxy and hydroxy; phenyl(lower)alkanoyl which may have 1 to 3 substituent(s) selected from the group consisting of lower alkoxy, aryl, halogen and mono(or di or tri)halo(lower)alkyl; phenyl(lower)alkenoyl; phenylthio(lower)alkanoyl; phenylcarbamoyl; phenylthiocarbamoyl; phenylglyoxyloyl which may have 1 to 3 substituent(s) selected from the group consisting of mono(or di or tri)halo(lower)alkyl and lower alkoxy; carbamoyl which may have one or two suitable substituent(s) selected from the group consisting of lower alkyl, hydroxy(lower)alkyl, acyloxy(lower) alkyl, lower alkoxy and cyclo(lower)alkyl; morpholinylcarbonyl; indolyl(lower)alkanoyl; morpholinyl (lower)alkanoyl; or piperidylcarbamoyl.

4. A compound of claim 3, wherein $R^1$ is halophenyl or pyridyl, $R^2$ is halophenyl, pyridyl, halopyridyl or lower alkoxypyridyl, $R^4$ is hydrogen; lower alkyl; cyclo(lower)alkyl; cyclo (lower)alkyl-(lower)alkyl; carboxy(lower)alkyl; lower alkoxycarbonyl(lower)alkyl; mono(or di)halophenyl (lower)alkyl; adamantanyl; phenyl(lower)alkenyl; tetrahydropyranyl; lower alkylpiperidyl; lower alkanoylpiperidyl; di(lower)alkyldioxaspiroundecanyl; indanyl; lower alkanoyl which may have a substituent selected from the group consisting of carboxy, esterified carboxy, lower alkoxy, halogen, lower alkoxycarbonylamino, lower alkanoylamino, amino, hydroxy, acyloxy and di(lower)alkylamino; lower alkoxycarbonyl; lower alkoxyglyoxyloyl; lower alkylsulfonyl; cyclo(lower)alkylcarbonyl; benzoyl which may have one or two substituent(s) selected from the group consisting of trihalo(lower)alkyl, halogen, acyloxy and hydroxy; phenyl(lower)alkanoyl which may have one or two substituent(s) selected from the group consisting of lower alkoxy, phenyl, halogen and trihalo (lower)alkyl; phenyl(lower)alkenoyl; phenylthio (lower)alkanoyl; phenylcarbamoyl; phenylthiocarbamoyl; phenylglyoxyloyl which may have a substituent selected from the group consisting of trihalo (lower)alkyl and lower alkoxy; carbamoyl which may have one or two suitable substituent(s) selected from the group consisting of lower alkyl, hydroxy(lower) alkyl, acyloxy(lower)alkyl, lower alkoxy and cyclo (lower)alkyl; morpholinylcarbonyl; indolyl(lower) alkanoyl; morpholinyl(lower)alkanoyl; or piperidylcarbamoyl.

5. A compound of claim 4, wherein $R^4$ is hydrogen; lower alkyl; cyclo(lower)alkyl; cyclo (lower)alkyl-(lower)alkyl; carboxy(lower)alkyl; lower alkoxycarbonyl(lower)alkyl; mono(or di)halophenyl (lower)alkyl; adamantanyl; phenyl(lower)alkenyl; tetrahydropyranyl; lower alkylpiperidyl; lower alkanoylpiperidyl; di(lower)alkyldioxaspiroundecanyl; indanyl; lower alkanoyl which may have a substituent selected from the group consisting of carboxy, esterified carboxy, lower alkoxy, halogen, lower alkoxycarbonylamino, lower alkanoylamino, amino, hydroxy, lower alkanoyloxy, cyclo(lower) alkylcarbonyloxy and di(lower)alkylamino; lower alkoxycarbonyl; lower alkoxyglyoxyloyl; lower alkylsulfonyl; cyclo(lower)alkylcarbonyl; benzoyl which may have one or two substituent(s) selected from the group consisting of trihalo(lower)alkyl, halogen, lower alkanoyloxy and hydroxy; phenyl(lower)alkanoyl which may have one or two substituent(s) selected from the group consisting of lower alkoxy, phenyl, halogen and trihalo(lower)alkyl; phenyl(lower)alkenoyl; phenylthio(lower)alkanoyl; phenylcarbamoyl; phenylthiocarbamoyl; phenylglyoxyloyl which may have a substituent selected from the group consisting of trihalo (lower)alkyl and lower alkoxy; carbamoyl which may have one or two suitable substituent(s) selected from the group consisting of lower alkyl, hydroxy(lower) alkyl, acyloxy(lower)alkyl, lower alkoxy and cyclo (lower)alkyl; morpholinylcarbonyl; indolyl(lower) alkanoyl; morpholinyl(lower)alkanoyl; or piperidylcarbamoyl.

6. A compound of claim 5, wherein $R^1$ is halophenyl, $R^2$ is pyridyl, $R^3$ is hydrogen, $R^4$ is phenylglyoxyloyl, and $R^5$ is hydrogen.

7. A compound of claim 6, which is selected from the group consisting of (1) 7-(4-Fluorophenyl)-2-phenylglyoxyloyl-8-(pyridin-4-yl)-1,2,3,4-tetrahydropyrazolo[5,1-c][1,2,4]triazine, (2) 7-(4-Fluorophenyl)-2-phenylglyoxyloyl-8-(pyridin-4-yl)-1,2,3,4-tetrahydropyrazolo[5,1-c][1,2,4]triazine hydrochloride, and (3) 7-(4-Fluorophenyl)-2-phenylglyoxyloyl-8-(pyridin-4-yl)-1,2,3,4-tetrahydropyrazolo[5,1-c][1,2,4]triazine sulfate.

8. A pharmaceutical composition which comprises, as an active ingredient, an effective amount of a compound of claim 1 or a pharmaceutically acceptable salt thereof in admixture with pharmaceutically acceptable carriers.

9. A method for the prophylactic or therapeutic treatment of Interleukin-1 (IL-1) and tumor necrosis factor (TNF) mediated diseases which comprises administering a compound of claim 1 or a pharmaceutically acceptable salt thereof to human or animals.

10. A process for preparing a pharmaceutical composition which comprises admixing a compound of claim 1 or a pharmaceutically acceptable salt thereof with a pharmaceutically acceptable carrier.

11. A method of inhibiting the production of Interleukin-1 (IL-1) and tumor necrosis factor (TNF) comprising contacting cells with an effective amount of a compound of claim 1 or a pharmaceutically acceptable salt thereof.

12. A process for preparing a compound of the formula:

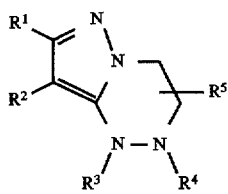

wherein $R^1$ is optionally substituted aryl, or optionally substituted saturated or unsaturated, monocyclic or polycyclic heterocyclic group containing at least one hetero-atom selected from the group consisting of oxygen, sulfur, and nitrogen atoms, $R^2$ is optionally substituted aryl, or optionally substituted saturated or unsaturated, monocyclic or polycyclic heterocyclic group containing at least one hetero-atom selected from the group consisting of oxygen, sulfur, and nitrogen atoms, $R^3$ is hydrogen or acyl, $R^4$ is hydrogen, lower alkyl, cyclo(lower)alkyl, cyclo(lower)alkyl-(lower)alkyl, carboxy(lower)alkyl, protected carboxy(lower)alkyl, ar(lower)alkyl which may have suitable substituent(s), ar(lower)alkenyl, bridged tricyclicalkyl, optionally substituted saturated or unsaturated, monocyclic or polycyclic heterocyclic group containing at least one hetero-atom selected from the group consisting of oxygen, sulfur, and nitrogen atoms, optionally substituted dioxaspiroundecanyl, acyl, or a group of the formula:

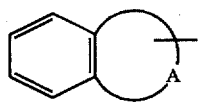

(in which A is lower alkylene), and $R^5$ is hydrogen or lower alkyl, or a salt thereof, which process comprises subjecting a compound of the formula:

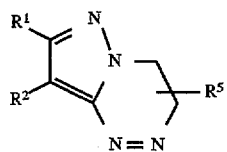

wherein $R^1$, $R^2$ and $R^5$ are each as defined above, or a salt thereof to reduction reaction to give a compound of the formula;

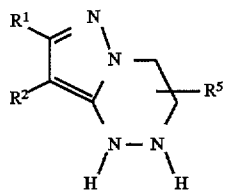

wherein $R^1$, $R^2$ and $R^5$ are each as defined above, or a salt thereof or (2) subjecting a compound of the formula:

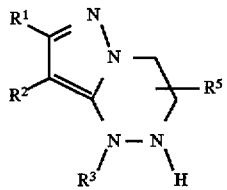

wherein $R^1$, $R^2$, $R^3$ and $R^5$ are each as defined above, or a salt thereof to acylation reaction to give a compound of the formula:

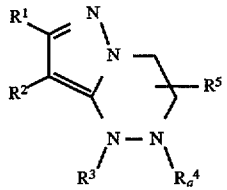

wherein $R^1$, $R^2$, $R^3$ and $R^5$ are each as defined above, and $R_a^4$ is acyl or a salt thereof.

* * * * *